US009803184B2

(12) United States Patent
Boschetti et al.

(10) Patent No.: US 9,803,184 B2
(45) Date of Patent: Oct. 31, 2017

(54) METHOD FOR IMMOBILIZING NUCLEIC LIGANDS

(75) Inventors: Egisto Boschetti, Croissy-sur-Seine (FR); Gérald Perret, Choisy le Roi (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 38 days.

(21) Appl. No.: 13/976,557

(22) PCT Filed: Dec. 30, 2011

(86) PCT No.: PCT/IB2011/056028
§ 371 (c)(1),
(2), (4) Date: Sep. 9, 2013

(87) PCT Pub. No.: WO2012/090183
PCT Pub. Date: Jul. 5, 2012

(65) Prior Publication Data
US 2013/0344567 A1 Dec. 26, 2013

(30) Foreign Application Priority Data

Dec. 30, 2010 (FR) .................................... 10 61366
Oct. 24, 2011 (FR) .................................... 11 59604

(51) Int. Cl.
C07H 21/00 (2006.01)
C12Q 1/68 (2006.01)
C12N 9/64 (2006.01)
B01J 20/289 (2006.01)
C07H 21/02 (2006.01)
C07H 21/04 (2006.01)
C07K 1/22 (2006.01)
B01J 20/32 (2006.01)

(52) U.S. Cl.
CPC .......... *C12N 9/6437* (2013.01); *B01J 20/289* (2013.01); *B01J 20/3204* (2013.01); *B01J 20/3212* (2013.01); *B01J 20/3219* (2013.01); *B01J 20/3274* (2013.01); *B01J 20/3278* (2013.01); *C07H 21/02* (2013.01); *C07H 21/04* (2013.01); *C07K 1/22* (2013.01)

(58) Field of Classification Search
None
See application file for complete search history.

(56) References Cited

U.S. PATENT DOCUMENTS

| | | | | | |
|---|---|---|---|---|---|
| 5,427,779 | A | * | 6/1995 | Elsner | C08J 7/12 424/490 |
| 5,756,291 | A | * | 5/1998 | Griffin et al. | 435/6.11 |
| 6,037,124 | A | * | 3/2000 | Matson | 435/6.12 |
| 2005/0106606 | A1 | * | 5/2005 | Parker et al. | 435/6 |
| 2006/0110594 | A1 | * | 5/2006 | Frutos et al. | 428/332 |
| 2009/0053169 | A1 | * | 2/2009 | Castillo | A61K 31/7105 424/85.2 |
| 2009/0258440 | A1 | * | 10/2009 | Bunch | G01N 33/54353 436/518 |
| 2009/0324723 | A1 | * | 12/2009 | Rawlin et al. | 424/489 |

FOREIGN PATENT DOCUMENTS

| | | |
|---|---|---|
| JP | 2005-283572 A | 10/2005 |
| WO | WO-2005/031305 A2 | 4/2005 |
| WO | WO 2009/024726 A1 | 2/2009 |

OTHER PUBLICATIONS

Saeki et al, Curr. Res. Tech. Ed. Appl. Microbiol. Microb. Biotech., pp. 188-195 (2010).*
Allerson et al., "A High-capacity RNA Affinity Column For the Purification of Human IRP1 and IRP2 Overexpressed in Pichia Pastoris," RNA, vol. 9, pp. 364-374, Mar. 1, 2003.
Goss et al., "High-performance affinity chromatography of DNA," Journal of Chromatography, vol. 508, pp. 279-287, Jan. 1, 1990.
Romig et al., "Aptamer affinity chromatography: combinatorial chemistry applied to protein purification," J. Chromatogra. B Biomed Sci Appl, 1999, 731(2): 275-284.
Madru et al., "Determination of Cocaine in Human Plasma by Selective Solid-Phase Extraction Using an Aptamer-Based Sorbent," Anal. Chem., vol. 81 : 7081-7086, 2009.
Caputi et al., "hnRNP A/B proteins are required for inhibition of HIV-1 pre-mRNA splicing," The EMBO Journal, vol. 18(14): 4060-4067, 1999.
Rehder et al., "Open-tubular capillary electrochromatography of bovine β-lactoglobulin variants A and B using an aptamer stationary phase," Electrophoresis, vol. 22(17): 3759, 2001.
Larson et al., "A high-capacity column for affinity purification of sequence-specific DNA-binding proteins," Nucleic Acids research, vol. 20(13): 3525, 1992.
Ruta et al., "Covalently bonded DNA apatmer chiral stationary phase for the chromatographic resolution of adenosine," Anal. Bioanal. Chem., vol. 390: 1051-1057, 2008.
Greco et al., "Synthesis and site-specific incorporation of a simple fluorescent pyrimidine," Nature Protocols, vol. 2, No. 2, pp. 305-316, 2007.
Hermanson, "Nucleic Acid and Oligonucleotide Modification and Conjugation," Bioconjugate Techniques, 2nd Edition, Academic Press, San Diego, Chapter 27, p. 970, 2008.
International Search Report issued in application No. PCT/IB2011/056028 dated Mar. 27, 2012.
Dynabeads M-270 Carboxylic Acid, Invitrogen Dynal SA, 2007, 2 pages.

(Continued)

Primary Examiner — Robert T Crow
(74) Attorney, Agent, or Firm — Potomac Law Group, PLLC; Rouget F. Henschel

(57) ABSTRACT

The invention relates to a method for immobilizing nucleic ligands including at least one reactive amine function, by grafting on an activated solid substrate, including a step of coupling said nucleic acids on said activated solid substrate having a pH of less than 6.

7 Claims, 5 Drawing Sheets

(56) References Cited

OTHER PUBLICATIONS

Dynal Biotech Product Catalogue 2005-2006, Cellular and Molecular Biology.

Kojima et al., "PCR amplication from single DNA molecules on magnetic beads in emulsion: application for high-throughput screening of transcription factor targets," Nucleic Acids Research, vol. 33, No. 17, 2005, 9 pages.

Wittebolle et al., "Optimisation of the amino-carboxy coupling of oligonucleotides to beads used in liquid arrays," Journal of Chemical Technology and Biotechnology, vol. 81, 2006, pp. 476-480.

"Instructions: Pierce NHS-Activated Agarose Dry Resin", Thermo Scientific, 2014, 4 pages.

\* cited by examiner

METHOD FOR IMMOBILIZING NUCLEIC LIGANDS

FIELD OF THE INVENTION

The invention relates to the field of the purification of substances of interest by means of affinity supports usable on an industrial scale, in particular for obtaining purified substances of medical interest.

PRIOR ART

There is a recurrent need for affinity chromatography supports which enable the selective enrichment of a starting product with a substance of interest. In the medical field, affinity chromatography supports are used to purify substances that are subsequently used as medicament active ingredients. Immunoaffinity chromatography supports on which antibodies are immobilized are mainly used. Immunoaffinity supports are suitable for purification of substances of medical interest on an industrial scale since they have a good retention capacity and a high selectivity with respect to their target molecule. Such immunoaffinity supports can be regenerated at the end of the purification processes without substantial impairment of their retention capacity or of their selectivity, thereby enabling them to be used over a long period of time. Furthermore, owing to their high retention capacity, immunoaffinity supports enable the purification of large amounts of the target substance, thereby making their use compatible with the technical and economic requirements of medicament production. However, immunoaffinity supports have drawbacks when they are used to purify substances of medical interest, owing in particular (i) to the release of immunogenic protein fragments derived from the antibodies immobilized during the phase of elution of the target substance previously retained and (ii) to the fragility of the antibodies with respect to the elution conditions and the periodic antibacterial and antiviral sanitization treatments.

Various studies have been undertaken in order to find alternatives to the known immunoaffinity supports. A limited number of studies concern the use of aptamers as affinity ligands for purifying target substances, including target proteins. By way of example, mention may thus be made of the studies by Romig et al. (J. Chromatogra. B Biomed Sci Appl, 1999, 731(2):275-84) which concern the purification of L-selectin on a chromatography support on which anti-L-selectin DNA aptamers have been immobilized via the streptavidin-biotin pairing.

It has been known for a long time that the affinity and the specificity of aptamers for their target molecule can be as high as those of antibodies. Moreover, since aptamers can be obtained by chemical synthesis, their production cost is much lower than that of antibodies. Nevertheless, the use of aptamer affinity supports for purifying target substances is at the current time peripheral despite the numerous economic and technical advantages exhibited by aptamers as affinity ligands. To the knowledge of the applicant, at the current time, no industrial process for purifying a target substance, including a target protein, comprises a step based on the use of an aptamer affinity support.

One reason which can be put forward to explain this lack of use of aptamers in industrial-scale purification processes is the difficulty in obtaining affinity supports on which the aptamers are stably and quantitatively attached.

The main technique for immobilizing aptamers which is described in the prior art is based on the use of the biotin-streptavidin or biotin-avidin pairing. This technique takes advantage of the selectivity and the strong affinity of biotin for its avidin or streptavidin ligand and also of the stability of the noncovalent complex resulting from their association. However, this type of affinity support has technical limitations resulting from the protein nature of the coupling agents used and from the noncovalent nature of the bond formed between the support and the aptamers. Indeed, biotin and avidin or streptavidin are sensitive to treatments capable of inducing protein denaturation. Moreover, the biotin/streptavidin complex dissociates at low temperature, in particular in nonionic or low-salt-concentration aqueous solutions. For these various reasons, affinity supports on which nucleic aptamers are immobilized as ligands by means of the biotin/streptavidin complex are not suitable for use in purification processes, in particular industrial purification processes, for which the possibility of regenerating and sanitizing the affinity supports between each purification cycle is essential.

The prior art also describes several techniques for the covalent grafting of nucleic acids onto solid supports, essentially with the objective of having new tools for carrying out analytical methods. The grafting of nucleic aptamers having a reactive amine group onto a sepharose support activated with cyanogen bromide has thus been described (Madru et al., 2009, Anal. Chem., Vol. 81: 7081-7086). The grafting of periodate-oxidized RNA aptamers onto an agarose support activated with adipic acid dihydrazide groups has also been described (Caputi et al., 1999, The EMBO Journal, Vol. 18(14): 4060-4067). Techniques for grafting nucleic aptamers by means of bifunctional coupling agents such as SIAB are also known (Rehder et al., Electrophoresis, Vol. 22(17): 3759).

The prior art also discloses techniques for covalent coupling of nucleic acids, inter alia of aptamers, on solid supports of silica or agarose type comprising carboxylic acid groups preactivated with N-hydroxysuccinimide (NHS) (Goss et al., 1990, J Chromatogr, Vol. 508: 279-287; Larson et al., 1992, Nucleic Acids research, Vol. 20(13): 3525, Allerson et al., 2003, RNA, Vol. 9: 364-374). These coupling techniques consisted of a direct application of the techniques conventionally used for the coupling of proteins on solid supports.

Goss et al. (1990, J Chromatogr, Vol. 508: 279-287) have thus described the grafting of a 5'-aminoethyl-poly(dT)$_{18}$ oligonucleotide onto a macroporous support of silica preactivated with NHS in a sodium phosphate buffer at pH=7.4. The affinity support obtained by Goss et al. has a degree of gaffing of poly(dT)$_{18}$ of 0.5 µmol per g of silica, which is very low given the number of carboxylate groups per g of silica gel (500 µmol per g of silica). In other words, only 0.1% of the carboxylate groups present at the surface of the support are bonded via an amide bond to a poly(dT)$_{18}$ oligonucleotide. Goss et al. have managed to capture a small amount of a mixture of model oligo-(dA)$_{12-18}$ nucleic acids with the resulting affinity support, and then to successively elute them in a salinity-gradient elution buffer.

In their article published in 2003, Allerson et al. (2003, RNA, Vol. 9: 364-374) deplored the fact that chromatography based on the use of nucleic acids as affinity ligand is rarely used for industrial-scale protein purification owing to the low capacity and/or the low stability of the affinity supports obtained to date. To the knowledge of these authors, the known coupling methods make it possible at the very most to immobilize only a few nanomoles of RNA per milliliter of support. According to a process analogous to that of Goss et al., Allerson et al. (2003, RNA, Vol. 9:

364-374) have described an attempt to couple nucleic aptamers, directed against an IRP1 or IRP2 regulatory protein, on an NHS-preactivated agarose support. Allerson et al. referred to the "recommendations of the manufacturer of the agarose support" for the implementation of this coupling and therefore carried out the coupling reaction at a basic pH equal to 8.3. It is specified that the manufacturer recommends, still today, carrying out the coupling of a ligand on an NHS-preactivated support at a pH of between 6 and 9 (see, for example, instructions document No. 71-5000-14 AC from GE Healthcare concerning the NHS-activated Sepharose 4 Fast Flow gel). Allerson et al. have themselves observed that the reaction for coupling RNA aptamers which have a primary amine function with an NHS-preactivated support gives a very low coupling yield, of about 2%, regardless of the coupling reaction time or the type of buffer solutions used, without managing to overcome this technical drawback. Allerson et al. (2003, above), finally moved away from this grafting technique in favor of a multistep grafting technique comprising (i) the introduction of alkyl thiol functions onto the support, (ii) the introduction of the 5'-iodoacetamide group in the 5' position of the aptamers by means of the Sulfo-SIAB bifunctional agent, and (iii) a step of actual coupling between the thiol functions of the support and the iodoacetamide groups of the aptamers so as to create a thiol bond. In the same way, Ruta et al. (2008, Anal. Bioanal. Chem., Vol. 390: 1051-1057) have shown that the stationary phase resulting from the rafting of DNA aptamers directed against D-adenosine onto an NHS-activated silica support has a very low binding capacity for D-adenosine.

There is therefore a need in the prior art for new methods for preparing affinity supports, in particular affinity supports suitable for the industrial-scale purification of substances of medical interest.

SUMMARY OF THE INVENTION

The present invention relates to a process for immobilizing nucleic acids comprising at least one reactive amine function, by grafting onto a solid support which has activated carboxylic groups at its surface, said process comprising a step of coupling said nucleic acids on said activated solid support at a pH of less than 6.

According to an alternative definition, the present invention relates to a process for immobilizing nucleic ligands comprising at least one primary amine function on a solid support, comprising the following steps:

a) providing a solid support comprising activated carboxylic acid groups at its surface, b) providing a nucleic ligand comprising at least one primary amine function, and c) carrying out the coupling of said nucleic acid with the activated carboxylic acid groups present at the surface of said solid support under conditions where the pH is less than 6, it being understood that the order of steps a) and b) makes no difference.

In one preferred embodiment, the activated carboxylic acid groups are obtained by reaction with N-hydroxysuccinimide or a derivative thereof.

The invention also relates to a method for preparing an affinity support, comprising the implementation of the immobilization process as defined above.

Another subject of the invention is a solid affinity support which can be obtained by means of the preparation method as defined above, and also the use thereof in processes for purifying or detecting a target protein.

An additional subject is a complex resulting from the interaction of a nucleic ligand and of a target molecule, said complex being formed at the surface of a solid support as previously defined.

Finally, the present invention also relates to a process for purifying a target ligand with an affinity support, comprising the following steps:

a) bringing a composition to be purified, comprising a target ligand of interest, into contact with an affinity support as defined above, in order to form a complex between (i) the nucleic acids grafted onto said support and (ii) said target ligand, and b) releasing said target ligand from the complex formed in step a) and recovering said purified target ligand.

DETAILED DESCRIPTION OF THE INVENTION

Figure 1:
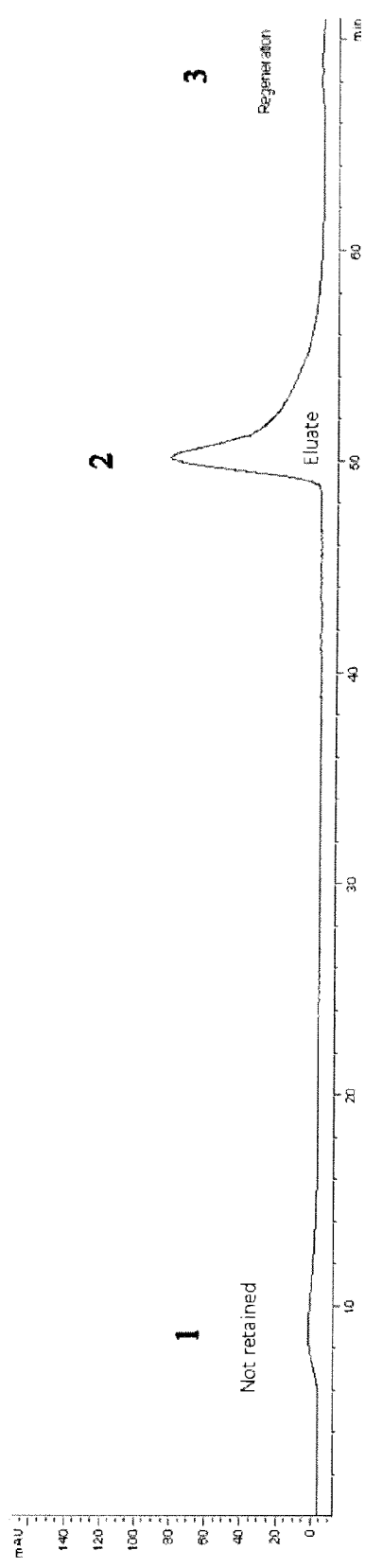
FIG. 1 shows a chromatographic profile obtained by passing a composition comprising 100 µg of transgenic human Factor VII over a solid support of the invention onto which anti-human FVII DNA aptamers have been grafted. Peak No. 1 corresponds to a fraction of human FVII not retained on the affinity support. Peak No. 2 corresponds to the human FVII contained in the elution fraction. Peak No. 3 corresponds to the human FVII contained in the regeneration eluent. Along the x-axis: the time, expressed in minutes. Along the y-axis: the absorbance, expressed in units of Optical Density at the wavelength of 280 nanometers.

The present invention provides novel affinity supports comprising immobilized nucleic acids, and also processes for preparing same.

A first subject of the invention is a process for immobilizing nucleic acids having at least one reactive amine function on a solid support having activated carboxylic acid functions.

According to the invention, the term "nucleic acid" or "nucleic ligand" is intended to mean a compound comprising a polymer of nucleotides or polynucleotide, i.e. of ribonucleotides and/or of deoxyribonucleotides which are optionally chemically modified, having a length ranging from 5 to 10 000 nucleotides, preferably a length ranging from 5 to 1000 nucleotides, and even better still from 5 to 120 nucleotides. A nucleic acid conventionally encompasses polyribonucleotides (RNAs) and polydeoxyribonucleotides (DNAs), where appropriate chemically modified.

A nucleotide is composed (i) of a (mono-, di- or tri-) phosphate group or an analog, (ii) of a sugar chosen from ribose and deoxyribose and chemical analogs thereof, and (iii) of a nitrogenous base chosen from adenine, guanine, thymine, cytosine and uracil, and chemical analogs thereof. For the purposes of the invention, a nucleotide can be modified both on its monosaccharide part and on its nitrogenous base by methods well known to those skilled in the art. By way of example, reference may be made to U.S. Pat. No. 5,958,691 which describes aptamers that have a chemical modification on one or more nucleotides. In certain embodiments, a nucleic acid consists of a polymer of nucleotides, ribonucleotides or deoxyribonucleotides.

In other embodiments, a nucleic acid consists essentially of a polymer of nucleotides and comprises a non-nucleotide part, said non-nucleotide part being preferentially of reduced length, compared with the length of the nucleotide part, for example a linear length less than the length occupied by a chain of five nucleotides, ribonucleotides or deoxyribonucleotides.

According to the invention, a nucleic acid comprises a reactive amine function when said nucleic acid has an amine function that is accessible to the solvent and capable of reacting with an appropriate reactive group borne by another molecular entity. The reactive amine functions encompass in particular primary amines. This primary amine is distinct from the aromatic amines borne by the purine or pyrimidine rings of the nucleotides.

Such nucleic acids are well known in the prior art and are conventionally used for their chemical coupling to supports or to label substances. Conventionally, they are nucleic acids which have been modified via the addition of an amine function at their 3' end or at their 5' end. Most commonly, the amine function is added at the 5' end of the nucleic acid, where its incorporation is easier as the final step of a process for synthesizing a polynucleotide. In certain embodiments, the reactive amine function and the 5' or 3' end of the nucleic acid are separated by a spacer chain.

According to the invention, a nucleic acid can comprise a reactive amine function at its 3' or 5' end, which means that the reactive amine function is coupled to the nucleotide part of said nucleic acid.

According to other embodiments, a nucleic acid can comprise a reactive amine function "on the side" of its 3' or 5' end, which means that said amine function is not directly coupled to the nucleotide part of said nucleic acid, but is covalently bonded to a non-nucleotide part of said nucleic acid, for example a non-nucleotide spacer chain which is interposed between said reactive amine function and said end of the nucleotide part of said nucleic acid.

In summary, for the purposes of the invention, a "nucleic acid", also denoted in the subsequent text as "nucleic ligand", comprises:

a polynucleotide, said polynucleotide consisting of a series of optionally chemically modified ribonucleotides and/or deoxyribonucleotides, and as an option, a non-nucleotide part, preferably a spacer chain.

Said nucleic ligand or acid also comprises a reactive amine function, it being possible for said reactive amine function to be attached either to a 3' or 5' end of the polynucleotide or, where appropriate, to the spacer chain.

Generally, the polynucleotide is at least modified on the 3' or 5' nucleotide in order to introduce the reactive amine function directly or by means of a non-nucleotide part, in particular a spacer chain.

The nucleic acid can comprise a chemical entity in addition to those previously mentioned, for example a fluorophore or a chromophore.

Generally, the nucleic acid according to the invention is a ligand, i.e. it is capable of binding specifically to one or more target molecules. In the subsequent text, the terms "nucleic ligand" and "nucleic acid" will therefore be used without distinction. The target molecules encompass RNA molecules, DNA molecules, chemical molecules of organic or inorganic nature, peptides and proteins, whether they are human, animal, plant, viral or bacterial.

The applicant has shown that it is possible to prepare affinity supports on which nucleic acids (or nucleic ligands) are immobilized, said affinity supports being usable in preparative techniques for purifying substances of therapeutic interest, since they have both a good capacity for selective retention of the target substances and excellent resistance to regeneration treatments, and their use does not lead to the risk of introducing potentially toxic or immunogenic substances into the resulting purified preparation.

More specifically, it has been shown according to the invention that affinity supports based on nucleic acids can be prepared by chemical grafting of said nucleic acids onto a solid support comprising activated carboxylic acid functions, under specific grafting conditions which make it possible both to obtain a high grafting yield and to maintain the structural and functional integrity of the grafted nucleic acids.

The applicant has shown that, contrary to what the article by Goss et al. (1990, above) indicated, the technique of coupling a ligand comprising a reactive amine function on an NHS-preactivated support, which is commonly used for coupling proteins on a support, cannot be directly transposed for the grafting of nucleic acids onto a support.

The results of the examples show in particular that, by using the conventional coupling method carried out at a pH of between 6 and 9 with a variety of distinct nucleic acids, a grafting yield ranging from 0% to a maximum of 10% is obtained. The results of the examples confirm those obtained by Allerson et al. (2003, above), who in the end had opted for another coupling technique.

With the objective of seeking coupling methods alternative to the known methods, the applicant has tested conditions for coupling on an NHS-activated support under which the anionic charges borne by the nucleic acids are masked by the addition of a source of monovalent or divalent ions, in the case in point by the addition of $Mg^{2+}$, $Ca^{2+}$ and/or $Na^+$ ions. The results of the examples show that neutralizing the anionic charges borne by the nucleic acids and/or increasing the ionic strength by adding divalent or monovalent cations does not make it possible to increase the grafting yield, which remains within a range of from 0% to 10%. It is also shown that neutralizing the anionic charges borne by the nucleic acids by adding ionized macromolecules, such as a Polybrene®, makes it impossible to graft these nucleic acids.

Likewise, the applicant has tested the efficiency of a coupling using nucleic acids in which the reactive amine function and the 5' end of the polynucleotide are separated from one another by a positively charged spacer chain. The spacer chain consisted of a polyamide comprising at least one tertiary amine function. The results, not presented in the examples, showed that an excellent grafting yield, close to 100%, was obtained on the NHS-preactivated support. On the other hand, the applicant has shown that bringing the support thus grafted into contact with a solution at an alkaline pH of approximately 9-10 modifies the structure of the spacer chain and leads to the detachment of the nucleic acids from the support. Such a coupling technique, which allows an excellent coupling yield, therefore provides an affinity support which has proved to be unsuitable for use in industrial purification processes, said processes generally comprising drastic washing and/or microbial inactivation steps.

The technical solution which has finally been developed according to the invention has consisted in carrying out the reaction for coupling the nucleic acids on the N-hydroxysuccinimide-preactivated support under conditions where the pH is less than 6.

The technical solution of the invention is entirely surprising since, at an acid pH, those skilled in the art would normally have expected the coupling reaction not to take place at all, or at the very least to take place in such a low proportion that a very low grafting yield is obtained owing to the weak reactivity of the primary amines and to the degradation by hydrolysis of the nucleic acids, generally observed at acid pHs.

However, it has been shown in the examples that carrying out the step of coupling a nucleic acid on an NHS-preactivated support, under conditions where the pH is less than 5, makes it possible to obtain a grafted support with a grafting yield of at least 70%. The grafting yield is even approximately 100% when the coupling reaction is carried out at a pH of less than 4.5.

Just as surprisingly, it is shown that carrying out the coupling step at an acid pH does not affect the functional integrity of the nucleic acids, even though the high sensitivity of nucleic acids to acid pH conditions is well known to those skilled in the art.

Even more surprisingly, the applicant has shown that this coupling reaction—which leads to the formation of an amide bond between the solid support and the nucleic acid—is very rapid, this reaction generally being finished in less than one hour, independently of the reaction temperature. Moreover, the applicant has shown that carrying out the reaction at low temperature is not a prerequisite for preserving the functional integrity of the grafted ligands. In other words, the process for immobilizing nucleic ligands according to the invention can be carried out independently at low temperature or at room temperature.

It has also been shown in the examples that the nucleic acids grafted onto the support retain their chemical and physical integrity, owing to the fact that their functionality is intact. This aspect is illustrated in the examples by a support grafted with nucleic aptamers capable of binding to human Factor VII (hFVII). It is shown that the capability of said anti-hFVII nucleic aptamers is intact after they have been grafted, under acidic pH conditions, at low temperature or at room temperature, onto the NHS-preactivated support. The applicant has also shown that, when a nucleic aptamer capable of binding selectively to active human Factor VII forms comprising a correctly gamma-carboxylated Gla domain is used for the grafting, the grafted aptamer retains the capability of the nongrafted aptamer of discriminating between (i) the active forms of human Factor VII comprising a correctly gamma-carboxylated Gla domain and (ii) the nonactive forms of human Factor VII.

It has also been shown that the specific coupling conditions disclosed in the present description are suitable for the grafting of any type of nucleic acid, i.e. both DNA nucleic acids and RNA nucleic acids.

Furthermore, the examples show that the process of the invention results in the production of affinity supports having a high density of grafted nucleic acids and consequently allows the preparation of affinity supports having a high capacity for capturing target ligands, which are usable on an industrial scale. To the knowledge of the applicant, such supports have never been described in the prior art.

The combined characteristics of high selectivity with respect to a target ligand and high capacity for capturing said target ligand illustrate the compatibility of an affinity support obtained according to the process of the invention with use in a step for purifying target ligands on an industrial scale. It goes without saying that the process according to the present invention also allows the preparation of affinity supports intended for the detection of a target molecule.

A subject of the present invention is more specifically a process for immobilizing nucleic ligands comprising at least one reactive amine function, by grafting onto a solid support having activated carboxylic acid groups, said process comprising a step of covalent coupling of said nucleic acids on said solid support at a pH of less than 6.

According to another definition, the process for immobilizing nucleic ligands comprising at least one reactive amine function on a solid support according to the invention comprises the following steps:
 a) providing a solid support comprising activated carboxylic acid groups at its surface,
 b) providing a nucleic ligand comprising at least one reactive amine function, and
 c) carrying out the coupling of said nucleic ligand with the activated carboxylic acid groups present at the surface of said solid support under conditions where the pH is less than 6,
it being understood that the order of steps a) and b) makes no difference.

It goes without saying that the coupling step c) allows the creation of amide bonds between the solid support and the nucleic ligands, each amide bond resulting from the reaction between an activated carboxylic acid function of the support and a primary amine function present on the nucleic ligand.

According to the invention, the conditions for coupling at a pH of less than 6 encompass conditions for coupling at a pH of less than 5.5, less than 5, less than 4.9, less than 4.8, less than 4.7, less than 4.6, less than 4.5, less than 4.3.

In certain embodiments, the pH of the coupling step is included in a range of from 3 to 6, thereby encompassing a pH of 3.0, a pH of 3.1, a pH of 3.2, a pH of 3.3, a pH of 3.4, a pH of 3.5, a pH of 3.6, a pH of 3.7, a pH of 3.8, a pH of 3.9, a pH of 4.0, a pH of 4.1, a pH of 4.2, a pH of 4.3, a pH of 4.4, a pH of 4.5, a pH of 4.6, a pH of 4.7, a pH of 4.8, a pH of 4.9, a pH of 5.0, a pH of 5.1, a pH of 5.2, a pH of 5.3, a pH of 5.4, a pH of 5.5, a pH of 5.6, a pH of 5.7, a pH of 5.8 and a pH of 5.9.

Preferably, the pH of the coupling step is less than 4.5. In certain embodiments, the pH of the coupling reaction is included in a range of from 3.5 to 4.5.

As is illustrated in the examples, the coupling step can be carried out at a pH of approximately 4.2.

Preferably, the coupling is carried out in the presence of an aqueous buffered medium having a pH of less than 6. The buffered medium can be prepared from weak acids and/or bases of any type, insofar as the weak acid(s) and base(s) used are not capable of reacting during the coupling reaction. As is illustrated in the examples, it may be an aqueous solution of sodium acetate.

Without wishing to be bound by any theory, the applicant thinks that, under the acid pH conditions used for the coupling reaction, the nucleic acids to be grafted are in linear form, thereby promoting the accessibility of their reactive amine group to the solvent, and in particular promoting the reaction of said reactive amine group with an activated carboxylic acid group accessible at the surface of the solid support.

The term "activated carboxylic acid function" or "activated carboxylic acid group" is intended to mean a chemical function derived from the "carboxylic acid" function capable of reacting with a nucleophile. More specifically, the term "activated carboxylic acid function" is intended to mean a chemical function derived from the "carboxylic acid" function capable of reacting with a primary amine so as to form an amide bond. "Activated carboxylic acid" functions are well known to those skilled in the art and encompass acid chloride, mixed anhydride and ester functions.

In certain embodiments, the activated carboxylic acid functions are in the form of esters resulting from the reaction of said carboxylic acid functions with a compound chosen from the group constituted by 1-hydroxybenzotriazole (HOBt), HOAt and N-hydroxysuccinimide, or a derivative thereof.

In one preferred embodiment, the carboxylic acid groups of the support have been activated by reaction with N-hydroxysuccinimide or a derivative thereof such as N-hydroxysulfosuccinimide.

This means that the "activated carboxylic acid" groups of the solid support correspond to "N-succinimidyl ester" groups, or else groups which are called "succinimidyl ester" groups or "N-hydroxysuccinimide ester" groups, of formula (I) below, wherein R represents the branching of the solid support to which the ester function is attached:

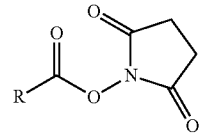

The activation with NHS or sulfo-NHS has the advantage of generating activated esters that react with primary amines but are also sufficiently stable to allow the packaging and storage of the preactivated support obtained.

Solid supports containing "activated carboxylic acid" functions are well known in the prior art and many of them are commercially available. The solid supports can also be prepared according to methodologies well known to those skilled in the art, for example by reacting a support initially having carboxylic acid functions at its surface with a suitable chemical agent allowing the activation of the carboxylic acid functions with a view to the subsequent formation of an amide bond. Reference may, in particular, be made to the conventional methods for activating carboxylic acid functions used in peptide synthesis, in particular via the solid process. By way of illustration, it is also possible to use, under the specific coupling conditions recommended by the invention, the methodology of activation by a combination of EDC (1-ethyl-3-[3-dimethylaminopropyl]carbodiimide hydrochloride) and NHS, well known to those skilled in the art.

The solid supports having "activated carboxylic acid" functions can be of any type. These supports encompass the supports conventionally used for chromatography, including silica and agarose supports, and which have been treated in order to have activated carboxylic acid groups at their surface. The preactivated solid supports encompass dextran, agarose or starch gels, cellulose derivatives, or else synthetic polymers such as polyamides, trisacryl, sephacryl, methacrylate derivatives, polystyrene derivatives and polyacrylamides, or else inorganic supports such as silica supports (in particular porous glass supports) or alumina supports, on the surface of which activated carboxylic acid groups are present. Generally, the solid supports on which the nucleic ligands according to the invention can be immobilized encompass any type of support having the structure and the composition commonly found for filter supports, membranes, etc. The solid supports encompass in particular resins, affinity chromatography column resins or gels, polymer beads, magnetic beads, paramagnetic beads, filtering membrane support materials, etc. The solid supports also encompass in particular materials based on glass or on metal, such as steel, gold, silver, aluminum, copper, silicon, glass or ceramic. The solid supports also encompass in particular polymer materials, such as a polyethylene, a polypropylene, a polyamide, a polyvinylidene fluoride, polyacrylamide derivatives and combinations thereof.

In the particular embodiments for which the carboxylic acid functions of the solid support are activated with NHS, said solid support can be obtained by reacting a commercial gel having free carboxylic acid functions with N-hydroxysuccinimide (NHS), optionally in the presence of a carbodiimide such as 1-ethyl-3-(3-dimethylaminopropyl)carbodiimide (EDC).

Use may also be made of an NHS-preactivated commercial solid support, for instance an "NHS Activated Sepharose 4 fast flow (GE)" gel sold by the company General Electric Healthcare (United States), a "HiTrap™ NHS-activated" gel sold by the company General Electric Healthcare (United States) or else an "NHS-Activated Agarose" gel sold by the company Thermo Scientific Pierce.

As is explained above, a nucleic ligand according to the invention comprises a polynucleotide, i.e. a polymer of nucleotides. The polynucleotide of the nucleic ligand is to a large extent responsible for the specific binding properties of said ligand with respect to its target molecule(s). It generally comprises from 5 to 120 nucleotides in length.

The nucleic ligand can also comprise a non-nucleotide part. Said non-nucleotide part is preferably bonded to the polynucleotide. The term "non-nucleotide part" is intended to mean a chemical unit which does not consist essentially of a polynucleotide. This non-nucleotide part is preferably a spacer chain. The reactive amine of said nucleic ligand is preferably a primary amine present at the 3' or 5' end of the polynucleotide or, where appropriate, a primary amine present at the level of the non-nucleotide part.

Preferably, the reactive amine is an aliphatic primary amine, which means that the amine function is not directly bonded to an aromatic group.

Thus, in some embodiments, the nucleic ligand is a polynucleotide from 5 to 120 nucleotides in length comprising at least one reactive amine function at its 3' or 5' end.

In other embodiments, the nucleic ligand comprises (i) a polynucleotide from 5 to 120 nucleotides in length and (ii) a spacer chain bonded to said polynucleotide, the reactive amine function being attached to a 3' or 5' end of said polynucleotide or to the spacer chain.

The spacer chain is preferentially bonded to the 5' end or to the 3' end of the nucleic acid.

In certain embodiments according to the invention, the nucleic ligand comprises a polynucleotide and a spacer chain, said spacer chain comprising an amine function at one of its ends and being bonded via its second end to the 5' end of the polynucleotide.

The function of said spacer chain is to physically distance the polynucleotide from the surface of the solid support, thereby making it possible to increase the relative mobility of the nucleotide part of the nucleic ligand and to reduce the steric hindrance.

The spacer chain may be of any type. The examples illustrate in particular the implementation of the process according to the invention for a hydrophobic chain consisting of a chain composed of a hydrophobic chain consisting of a chain composed of 3, 6, 12 or more (for example 18) methylenes ($CH_2$), subsequently known as C3, C6 or C12, or a hydrophilic chain which can be of polyethylene glycol type, for example hexaethylene glycol (HEG), or an 11-amino-3,6,9-trioxaundecan-1-yl, subsequently referred to as hydrophilic C11, or a nonspecific oligonucleotide. Preferably, the spacer chain does not comprise ionizable groups other than primary amine functions or secondary amine functions. Generally, the spacer chain does not comprise groups or bonds sensitive to alkaline pH or to oxidation or reduction reactions. In particular, the spacer chain does not contain any disulfide bond or thiol groups. The spacer chain essentially contains bonds of carbon-carbon, carbon-oxygen and carbon-nitrogen type. The spacer chain is preferably chosen from the group constituted by: a hydrophobic chain consisting of a chain composed of 3, 6, 12 or more (for example 18) methylenes ($CH_2$), subsequently referred to as C3, C6, C12, or a hydrophilic chain which can be of polyethylene glycol type, for example hexaethylene glycol (HEG), or an 11-amino-3,6,9-trioxaundecan-1-yl, subsequently referred to as hydrophilic C11, or a nonspecific oligonucleotide, substituted with a primary amine function.

Figure 2:
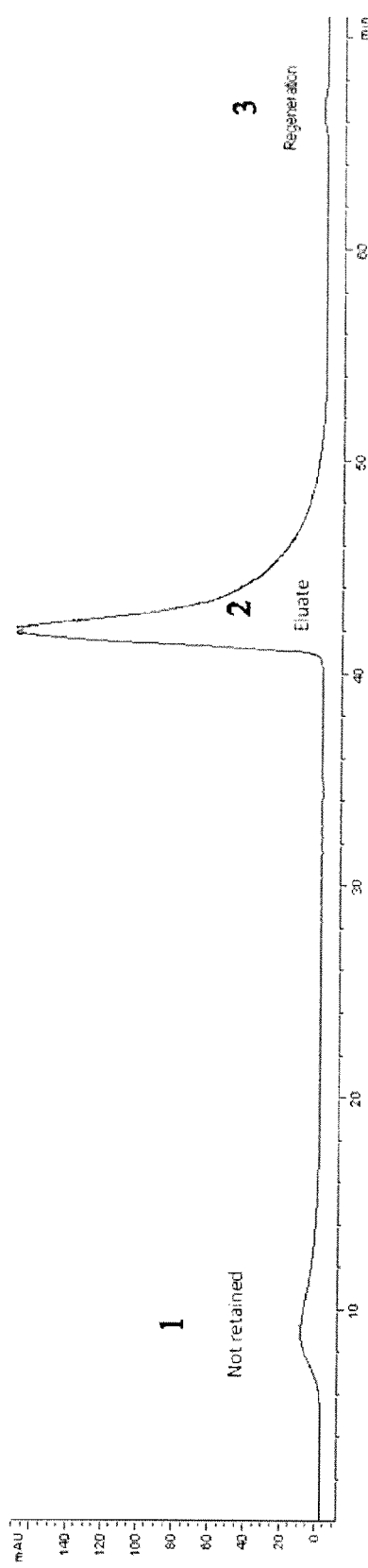
FIG. 2 shows a chromatographic profile obtained by passing a composition comprising 200 µg of transgenic human Factor VII over a solid support of the invention onto which anti-human FVII DNA aptamers have been grafted. Peak No. 2 corresponds to the human FVII contained in the elution fraction. Peak No. 3 corresponds to the human FVII contained in the regeneration effluent. Along the x-axis: the time, expressed in minutes. Along the y-axis: the absorbance, expressed in units of Optical Density at the wavelength of 280 nanometers.

The spacer chain can be introduced according to methods well known to those skilled in the art, in particular as a final step of the chemical synthesis of the polynucleotide. In this particular case, the spacer chain may be introduced at the 5' end of the polynucleotide by means of a derivative comprising a phosphoramidite function as is described in the examples. The general principle of this reaction is shown in FIG. 2 of Greco and Tor, Nature Protocols, 2007, 2, 305-316 entitled "Key steps in solid DNA phospharimidite synthesis cycle". It is also possible to introduce a molecule containing a primary amine in the 5' position of the polynucleotide by coupling a diamine such as ethylenediamine in the presence of EDC and of imidazole (see technical sheet No. TR0030.5 published by Thermo scientific). Reference may be made to the reference manual by Hermanson (Bioconjugate Techniques, 2008, 2nd Edition, Academic Press, San Diego) and in particular to chapter 27, p. 970.

As is illustrated in the examples of the present application, the coupling step can be carried out without distinction at low temperature and at room temperature. Notably, carrying out the reaction at room temperature does not produce a decrease in the reaction yield. In the same way, carrying out the reaction at low temperature—typically at a temperature of 5° C.—does not produce a substantial reduction in the reaction rate.

Thus, in certain embodiments, the coupling step is carried out at a temperature included in a range of from 0° C. to 50° C.

Preferably, the coupling step can be carried out at a temperature ranging from 0° C. to 35° C.

Practically, the coupling reaction may be carried out at room temperature, i.e. at a temperature ranging from 15° C. to 35° C., preferably at a temperature ranging from 15° C. to 25° C. Nevertheless, the coupling step may be carried out at low temperature, typically at a temperature ranging from 0° C. to 8° C., if the reagents involved—in particular the nucleic ligands—have chemical groups which are sensitive, in particular, to hydrolysis.

Since the coupling reaction is particularly fast, a satisfactory progression of the reaction is generally obtained after approximately one hour, or even after a few minutes. By using suitable kinetic monitoring techniques, those skilled in the art will be able to determine the optimum reaction time. The same is true for the reaction temperature.

Generally, as is illustrated in the examples, the coupling step can be carried out at a pH ranging from 3.5 to 4.5, at room temperature and over the course of a period of approximately one hour.

Of course, those skilled in the art can, on the basis of the general conditions above, adapt the coupling reaction conditions in order to determine the suitable optimum conditions in each precise case, on the basis of their general knowledge in chemistry. By way of illustration, those skilled in the art can easily predict that, in order to obtain a given coupling yield, reducing the reaction temperature is liable to require an increase in the duration of the coupling step.

In certain embodiments of the immobilization process according to the invention, the coupling reaction can be finished by placing the preactivated support/nucleic acids combination under alkaline pH conditions for a given period of time.

In these embodiments, the coupling step of the process of the invention itself comprises the following two steps:

c1) reacting said nucleic acid with the activated carboxylic acid groups present at the surface of said solid support, under conditions where the pH is less than 6, and c2) continuing the reaction for coupling said nucleic acid with the activated carboxylic acid groups present at the surface of said solid support, under conditions where the pH is greater than 7.5.

Without wishing to be bound by any theory, the applicant thinks that the implementation of substep c2) can, in certain specific cases, induce the nucleic acids immobilized on the support to adopt a suitable conformation. The applicant is of the opinion that this step is optional.

Advantageously, the final phase of coupling at alkaline pH is carried out at a pH of at least 7.5, which encompasses pHs of at least 8, and of at least 8.5. The examples illustrate the implementation of step c2) at a pH of approximately 9.

Step c2) can be carried out at room temperature or at a low temperature. The term "low temperature" for the final step of the coupling reaction is intended to mean a temperature of less than 15° C., including a temperature of less than 14° C., 13° C., 12° C., 11° C., 10° C., 9° C., 8° C., 7° C., 6° C. or 5° C.

The duration of the final phase of the coupling step is variable. It is between a few minutes and a few hours. Generally, the duration of step c2) is less than 9 hours, which encompasses a duration of less than 8, 7, 6, 5, 4, 3, 2 hours and 1 hour. The duration of step c2) can be approximately 8 hours or approximately 3 hours, as is illustrated in the examples.

For said final phase of the coupling step, those skilled in the art can easily, on the basis of the above indications, determine the optimum conditions for the combination of pH, temperature and duration, on a case-by-case basis.

In advantageous embodiments, the coupling reaction is followed by a step of neutralizing d) or blocking the activated carboxylic acid groups which have not reacted during the actual coupling step. By way of illustration, the blocking of the activated carboxylic acid functions which have not reacted can be carried out by incubating the grafted support with a blocking solution comprising 0.5M of ethanolamine, and 0.5M of NaCl at pH 8.3 or else with a blocking solution containing 0.1M Tris-HCl at pH 8.5, as is recommended in particular by the producer and described, moreover, in the examples. The duration of the neutralizing or blocking step is advantageously at least one hour at low temperature. It can be carried out, for example, for a period of 2 h30 at a temperature of 4° C., as described in the examples.

Lastly, the process according to the invention comprises, at the end of the coupling step c) and/or at the end of the blocking or neutralizing step d), one or more steps e) of washing said support under conventional conditions so as to obtain a ready-to-use affinity support. By way of illustration, the washing step(s) can be carried out with a buffer solution of 0.1M Tris-HCl at a pH ranging from 8 to 9, or else with a buffer solution of 0.1M acetate, 0.5M NaCl at a pH ranging from 4 to 5, as is illustrated in the examples. In certain embodiments, a washing step successively comprises (i) washing with a buffer solution of 0.1M Tris-HCl at a pH ranging from 8 to 9, followed by (ii) washing with a buffer solution of 0.1M acetate, 0.5M NaCl at a pH ranging from 4 to 5. Conventionally, a plurality of washing steps is carried out, for example 3 washing steps, as is illustrated in the examples.

In the light of the description above, the process for immobilizing nucleic acids according to the invention can also be defined as a process comprising the following steps:

a) providing a solid support comprising activated carboxylic acid groups, preferably activated with N-hydroxysuccinimide, at its surface, b) providing a nucleic acid comprising at least one primary amine function, c) carrying out the coupling of said nucleic acid with the activated carboxylic acid groups present at the surface of said solid support under conditions with a pH of less than 6, and d) blocking the coupling reaction.

The process for immobilizing nucleic acids according to the invention can also be defined as a process comprising the following steps:

a) providing a solid support comprising activated carboxylic acid groups, preferably activated with N-hydroxysuccinimide, at its surface, b) providing a nucleic acid comprising at least one primary amine function, c) carrying out the coupling of said nucleic acid with the activated carboxylic acid groups present at the surface of said solid support under conditions where the pH is less than 6, d) blocking the coupling reaction, and e) carrying out one or more support washing steps.

As has already been specified previously, in certain embodiments, step c) itself comprises the following two steps:

c1) reacting said nucleic acid with the activated carboxylic acid groups, preferably activated with N-hydroxysuccinimide, present at the surface of said solid support under conditions where the pH is less than 6, and c2) continuing the reaction for coupling said nucleic acid with the activated carboxylic acid groups present at the surface of said solid support under conditions where the pH is greater than 7.5.

The process for immobilizing the nucleic ligands according to the invention has a direct application in the production of affinity supports intended for the purification or detection of target molecules, including target proteins.

Thus, more generally, the present invention relates to a method for preparing an affinity support comprising the implementation of the process for immobilizing nucleic ligands as defined above. Thus, the method for preparing an affinity support according to the invention comprises the following steps:

a) providing a solid support comprising activated carboxylic acid groups at its surface, b) providing a nucleic ligand comprising at least one primary amine function, and c) carrying out the coupling of said nucleic ligand with the activated carboxylic acid groups present at the surface of said solid support under conditions where the pH is less than 6, it being understood that the order of steps a) and b) makes no difference.

Step c) of the method can comprise steps c1) and c2) as previously defined. In the same way, the method can also comprise steps d) and e) previously described.

As is illustrated in the examples, the method and the process according to the invention are particularly suitable for preparing an affinity support intended for the purification of one or more target molecules, in particular by chromatography.

Thus, in certain embodiments of the process according to the invention, the solid support is a support suitable for carrying out a chromatography, filtration or solid-phase extraction process. In other words, the solid support is suitable for use as a stationary phase in a chromatography or filtration or solid-phase extraction process. For the use of a solid affinity support for solid-phase extraction, reference may be made to Madru et al. (Analytical Chemistry, 2009, 81, 7081-7086). Such a solid support can be chosen from the group constituted by silica gels and polysaccharide gels, such as agarose gels, dextran gels and derivatives thereof and also acrylamide gels and derivatives thereof, methacrylate gels and derivatives thereof, and polystyrene surfaces and derivatives thereof.

Thus, in one particular embodiment of the immobilization process or method according to the invention, (i) the solid support comprising activated carboxylic acid groups at its surface is a support chosen from the group constituted by silica gels, agarose gels, dextran gels, and derivatives thereof, and (ii) the nucleic acid ligand comprising at least one reactive amine is chosen from the group of polynucleotides of 5 to 120 amino acids optionally comprising at their 3' or 5' end a spacer chain which can be chosen from the group constituted by a hydrophobic chain consisting of a chain composed of 3, 6, 12 or more (for example 18) methylenes ($CH_2$), subsequently referred to as C3, C6 or C12, or a hydrophilic chain which can be of polyethylene glycol type, for example hexaethylene glycol (HEG), or an 11-amino-3,6,9-trioxaundecan-1-yl, subsequently referred to as hydrophilic C11, or a nonspecific oligonucleotide.

In another particular embodiment of the process or of the method according to the invention, (i) the solid support is chosen from agarose gels and derivatives thereof, and (ii) the nucleic ligand is a polynucleotide of 5 to 120 nucleotides bonded, via its 5' end, to a spacer chain chosen from $C_4$-$C_{20}$ polyethylene glycols, the reactive amine function preferably being borne by the spacer chain.

In one additional embodiment of the process or of the method according to the invention, (i) the solid support is chosen from agarose gels and derivatives thereof, and (ii) the nucleic ligand is a polynucleotide of 5 to 120 nucleotides bonded, via its 5' end, to a spacer chain chosen from $C_4$-$C_{20}$ linear alkyls, the reactive amine function preferably being borne by the spacer chain.

The examples show that the affinity supports obtained according to the process of the invention allow the quantitative purification of a target ligand in an extremely selective manner.

Likewise, the results of the examples show that an affinity support obtained according to the process of the invention can be used over a very long period of time, in particular in a large number of capture/washing/elution/washing cycles without significant loss of its properties of selective and quantitative retention of the target ligand. It is also shown that an affinity support according to the invention retains its properties of selective and quantitative retention of the target ligand, even after having undergone drastic antibacterial, antifungal or antiviral regenerating or sanitizing steps. It has been shown, in particular, in the examples that the retention capacity of an affinity support according to the invention for its target protein is not impaired by treatment with a solution having a final concentration of NaOH of 0.5 M, nor even by treatment with a solution of NaOH having a final concentration of 1 M, i.e. a final concentration of NaOH much higher than that which is normally used during the sanitizing steps, for a very long period of time (100 hours), which is likewise much longer than the duration of a conventional sanitizing step, which is generally a few minutes. It has also been shown that the chromatographic properties of an affinity support according to the invention are not impaired by treatment with a solution having a final concentration of propylene glycol of 50% (vol/vol).

The results of the examples also show that the chromatographic properties of an affinity support according to the invention are not impaired, even after lengthy incubation of said support with the starting biological medium containing the molecule to be purified.

It is also shown in the examples that the chromatographic properties of an affinity support according to the invention are unchanged, even after numerous cycles of use.

In other words, the results of the examples illustrate the capacity of an affinity support according to the invention to entirely reproducibly perform quantitative target-ligand purification steps, under conventional industrial conditions for use, which are generally deleterious for the known affinity supports, including for immunoaffinity supports. The technical characteristics of each of the steps of the process of the invention, according to the various definitions above, have already been previously specified in the present description.

The affinity supports according to the invention thus constitute purification tools which are both reliable and reproducible, and stable over time, and do not require repeated maintenance operations. The affinity supports of the invention, owing to the numerous technical advantages that they provide, make it possible to carry out processes for purifying a target molecule at moderate costs.

The examples describe the obtaining of an affinity support of the invention by grafting of nucleic aptamers, and as an illustration by grafting of DNA aptamers.

Thus, in one preferred embodiment of the process or of the method according to the present invention, the nucleic ligand is a nucleic aptamer.

According to the invention, the term "nucleic aptamer" or "aptamer" is intended to mean a single-stranded nucleic acid which binds specifically to one or more target ligands. The aptamers encompass those for which it is possible to detect complexes with a single given target ligand or with a variety of given target ligands, after a prior step of bringing the respectively nucleic and target ligand partners into contact. The aptamers encompass RNA aptamers and DNA aptamers.

The term "aptamer" as it is used here denotes a single-stranded DNA or RNA nucleic acid molecule capable of binding specifically to one or more target ligands, such as a protein. Aptamers bind to their target molecules via mechanisms which are essentially distinct from hybridization. Aptamers are generally characterized by a secondary structure comprising loops and stems. In other words, the active conformation of aptamers (i.e. the conformation in which aptamers are capable of binding to their target protein) is nonlinear.

Aptamers generally comprise between 5 and 120 nucleotides and can be selected in vitro according to a process known as SELEX (Systematic Evolution of Ligands by Exponential Enrichment). Aptamers have many advantages. By virtue of their oligonucleotide nature, aptamers have a low immunogenicity and high resistance to stringent physicochemical conditions (presence of urea, of DMSO, of a very acid or of a very basic pH, use of organic solvents or of a high temperature) enabling varied sanitization strategies in the context of use as an affinity ligand. Furthermore, they have high selectivity. Finally, the production of aptamers involves relatively limited costs.

In some embodiments, a "nucleic aptamer" used for the grafting to the preactivated solid support, according to the process or the method defined above, can comprise, by definition, a non-nucleotide or nucleotide part, for example a non-nucleotide spacer chain, which links one of the 5' or 3' ends of the nucleic part of said aptamer and the reactive amine function used for the chemical grafting of said preactivated support. In these embodiments, a nucleic aptamer can be of formula (I) below:

  (I), in which:

n is an index equal to 1 or 0, 0 meaning that the aptamer does not comprise a free spacer chain and 1 meaning that the aptamer comprises a spacer chain, $NH_2$ means the reactive amine function used for the grafting onto the solid support preactivated with NHS groups,

[SPAC] means a spacer chain, and

[NUCL] means a nucleic acid which binds specifically to a target molecule, said nucleic acid comprising from 5 to 120 nucleotides.

Preferably, the nucleic acid [NUCL] comprises from 10 to 80 nucleotides and even more preferably from 20 to 60 nucleotides.

The "spacer chain" denoted [SPAC] in the compound of formula (I) can be of any known type. It can be a non-nucleotide compound, an oligonucleotide or a compound comprising one or more non-nucleotide parts and one or more nucleotide parts. The spacer chain does not generally participate in the binding of the target ligand to the support.

The function of said spacer chain is to physically distance the nucleic acid [NUCL] from the surface of the solid support onto which said compound of formula (I) is chemically grafted, thereby enabling a relative mobility of the nucleic acid [NUCL], relative to the surface of said solid support. The spacer chain limits or prevents steric hindrance, due to the proximity between the solid support and the nucleic part of the aptamer being too great, from impairing the binding events between said nucleic acid and target ligand molecules which may be brought into contact with said nucleic acid.

In the compound of formula (II), the spacer chain is preferentially bonded to the 5' end or to the 3' end of the nucleic acid [NUCL].

This construction with a spacer has the advantage of not directly immobilizing the aptamer on the solid support. Preferably, as was indicated above, the spacer chain can be a hydrophobic chain consisting of a chain composed of 3, 6, 12 or more (for example 18) methylenes ($CH_2$), subsequently referred to as C3, C6, C12, or a hydrophilic chain which can be of polyethylene glycol type, for example hexaethylene glycol (HEG), or an 11-amino-3,6,9-trioxaundecan-1-yl, subsequently referred to as hydrophilic C11, or a nonspecific oligonucleotide. When the spacer chain consists of a nonspecific oligonucleotide, said oligonucleotide advantageously comprises at least 5 nucleotides in length, preferably between 5 and 15 nucleotides in length.

In certain embodiments, the spacer chain may be composite and comprise the succession of HEG and of an oligonucleotide, for example an oligo(dT).

It is recalled that the examples illustrate the obtaining of affinity supports as defined above by grafting of the NHS-preactivated support with three distinct anti-FVII nucleic aptamers comprising spacer chains of nature which is likewise distinct, namely a hydrophobic chain consisting of a $C_6$ alkyl chain, a hydrophobic chain consisting of a $C_{12}$ alkyl chain, and a hydrophilic C11-TFA chain. Thus, the results of the examples show that the process for obtaining an affinity support which is described in the present description can be used regardless of the identity or the type of nucleic acid of interest to be grafted.

As was mentioned above, the processes and method according to the invention make it possible to prepare affinity supports which differ from the known affinity supports by virtue of their high density of nucleic ligands immobilized at their surface. This high density of nucleic ligands ensues directly from the specific process for obtaining the affinity supports.

Notably, the affinity supports according to the invention are also characterized by a high capacity for retention of the target molecule(s) against which the grafted nucleic acids are directed. In particular, the process according to the invention makes it possible to prepare affinity chromatography gels which have a high density of nucleic ligands. It has thus been observed that chromatography gels obtained by means of the process according to the invention have a nucleic ligand density of 0.2 µmol/ml to 0.5 µmol/ml, whereas the initial density of activated carboxylic acid functions of the chromatography gels that are commercially available is generally between 5 µmol/ml and 25 µmol/ml of gel. Thus, according to the coupling process of the invention, it is possible to derivatize, according to the process of the invention, at least 0.01% of the activated carboxylic functions initially present at the surface of the solid support, advantageously at least 0.1%, better still at least 1% and even better still at least 2% of said activated carboxylic functions. By way of comparison, the degrees of grafting in affinity chromatography with antibodies as ligand are often less than 1 mg/ml, i.e. less than 0.06 µmol/ml, i.e. less than 0.2% of derivatized carboxylic functions.

A derivatization of at least 0.01% of the activated carboxylic functions encompasses a derivatization of at least 0.05%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9% and at least 2% of said activated carboxylic functions.

In certain embodiments, the percentage of derivatized carboxylic functions is at most 100%, which encompasses at most 50%, 40%, 30% and at most 25% of said activated carboxylic functions.

Thus, another subject of the present invention is an affinity support which can be obtained in accordance with the process and with the method described above in the present description.

More generally, the present invention relates to a solid affinity support on which nucleic ligands are immobilized via an amide bond and in which at least carboxyl functions initially present at its surface are derivatized with a nucleic ligand.

It goes without saying that the amide bond bonding a nucleic ligand to the support is the result of the reaction of a carboxyl function initially present at the surface of the support with a primary amine function present on the nucleic ligand.

In one preferred embodiment, the solid affinity support is a chromatography gel.

Another subject of the present invention is a solid affinity support on which nucleic ligands are immobilized via an amide bond, said affinity support being a chromatography gel having a nucleic ligand density of at least 0.005 µmol/ml of gel, which encompasses at least 0.01 µmol/ml, 0.05 µmol/ml, 0.1 µmol/ml, 0.15 µmol/ml, 0.2 µmol/ml, 0.25 µmol/ml, 0.3 µmol/ml, 0.35 µmol/ml, and at least 0.38 µmol/ml of gel.

In certain embodiments, the nucleic ligand density is at most 10 mol/ml, which encompasses at most 5 µmol/ml, at most 1 µmol/ml and at most 0.5 µmol/ml.

The affinity supports according to the invention can have any one of the properties described above for the solid supports or the affinity supports.

Thus, in certain embodiments, the affinity support can be a gel usable in chromatography, in filtration or in solid-phase extraction, chosen from the group constituted by agarose gels, dextran gels and silica gels, and derivatives thereof.

As is illustrated in the examples, the affinity support can be a highly crosslinked agarose gel on which the nucleic ligands are immobilized. Preferably, the affinity support is a gel (in other words a stationary phase) usable in affinity chromatography processes.

The affinity supports according to the invention can comprise at their surface nucleic ligands of any type as described above in the present description.

In certain embodiments, the affinity support according to the invention is characterized in that the nucleic ligands are aptamers of formula (II) presented above.

In particular embodiments, the solid affinity support according to the invention can be represented by formula (III) below:

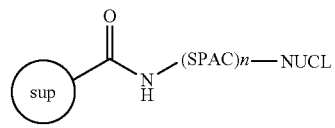

in which:
[SUP] represents the solid support of the affinity support,
[SPAC]n and [NUCL] correspond to the definitions previously indicated. In other words, —NH—(SPAC)$_n$-NUCL represents a nucleic aptamer in which:
n is an index equal to 0 or 1,
SPAC represents a spacer chain, and
NUCL represents a nucleic acid which binds specifically to a target molecule, said nucleic acid comprising from 5 to 120 nucleotides.

Another subject according to the invention is a complex formed between a nucleic ligand and a target molecule, said complex being formed at the surface of a solid support as previously defined. Said complex results essentially from noncovalent interactions between the target molecule and the nucleic ligand.

An additional subject of the invention relates to the use of an affinity support as previously described for purifying or detecting a target molecule. In the context of the purification of a target molecule, the support according to the invention can be used as a stationary phase in filtration, chromatography or solid-phase extraction steps.

The present invention also relates to a process for purifying a target molecule with an affinity support as defined above, comprising the following steps:

a) bringing a composition to be purified, comprising a target molecule of interest, into contact with an affinity support as defined in the present description, in order to form a complex between (i) the nucleic acids grafted onto said support and (ii) said target ligand, and b) releasing said target molecule from the complex formed in step a) and recovering said purified target molecule.

In one particular embodiment, the process comprises a step a'), the step a' following step a) and preceding step b), which consists of a step of washing the affinity support with a washing buffer.

It has also been shown in the examples that the use, in step a'), of a washing buffer having a high hydrophobicity, in particular a high concentration of propylene glycol, makes it possible to efficiently remove the substances bound nonspecifically to the affinity support without simultaneously detectably affecting the binding of the target ligand to the affinity support.

In step a'), a washing buffer having a final content of propylene glycol of at least 20% by volume, relative to the total volume of the buffer solution, is thus preferably used.

According to the invention, a washing buffer having a final content of propylene glycol of at least 20% encompasses washing buffers having a final content of propylene glycol of at least 25%, 30%, 35%, 40%, 45%, 50%, 55%, or at least 60% by volume, relative to the total volume of the buffer solution.

Preferably, a washing buffer used in step a') of the process has a final content of propylene glycol of at most 50%. Advantageously, a washing buffer used in step a') of the process has a final content of propylene glycol of between 20% and 50%, preferably between 30% and 50%.

According to one particular embodiment, the washing buffer used in step a') contains both NaCl and propylene glycol as described in the examples.

Furthermore, in certain embodiments of the purification process above, step b) is carried out by bringing the affinity support into contact with an elution buffer containing a divalent-ion-chelating agent, preferably EDTA.

By way of illustration, the elution buffer can contain a final concentration of EDTA of at least 1 mM and of at most 30 mM.

The expression "at least 1 mM" encompasses at least 2, 3, 4, 5, 6, 7, 8, 9 or 10 mM.

The expression "at most 30 mM" encompasses at most 29, 28, 27, 26, 25, 24, 23, 22, 21, 20, 19, 18, 17, 16, 15, 14, 13, 12 or 11 mM.

Advantageously, a buffer comprising a mixture of NaCl and propylene glycol, which may be of the same type as that described above for the washing step, is used for the regeneration of the affinity support.

For the purposes of the present invention and for the various subjects described above included in the invention, the term "target molecule" (or "target substance" or alternatively "target ligand") as used here denotes a molecule capable of binding specifically to the aptamer. It may be a question of nucleic acids, proteins or organic or inorganic substances. The proteins may be proteins of any type, and in particular plasma proteins.

According to the invention, the term "plasma protein" is intended to mean any protein, especially any protein of industrial or therapeutic interest, contained in blood plasma. The blood plasma proteins encompass antibodies, albumin, alpha-macroglobulin, antichymotrypsin, antithrombin, antitrypsin, Apo A, Apo B, Apo C, Apo D, Apo E, Apo F, Apo G, beta-XIIa, C1-inhibitor, C-reactive protein, C7, C1r, C1s, C2, C3, C4, C4bP, C5, C6, C1q, C8, C9, carboxypeptidase N, ceruloplasmin, Factor B, Factor D, Factor H, Factor I, Factor IX, Factor V, Factor VII, Factor VIIa, Factor VIII, Factor X, Factor XI, Factor XII, Factor XIII, fibrinogen, fibronectin, haptoglobin, hemopexin, heparin cofactor II, histidine rich GP, IgA, IgD, IgE, IgG, ITI, IgM, kininase II, HMW kininogen, lysozyme, PAI 2, PAI 1, PCI, plasmin, plasmin inhibitor, plasminogen, prealbumin, prokallikrein, properdin, protease nexin INH, protein C, protein S, protein Z, prothrombin, TFPI, thiol-proteinase, thrombomodulin, tissue factor (TF), TPA, transcobalamin II, transcortin, transferrin, vitronectin, and von Willebrand factor.

In particular, the plasma proteins encompass coagulation proteins, i.e. plasma proteins involved in the chain of cascade reactions resulting in the formation of a blood clot. The coagulation proteins encompass Factor I (fibrinogen), Factor II (prothrombin), Factor V (proaccelerin), Factor VII (proconvertin), Factor VIII (anti-hemophilic Factor A), Factor IX (anti-hemophilic Factor B), Factor X (Stuart Factor), Factor XI (Rosenthal Factor or PTA), Factor XII (Hageman Factor), Factor XIII (fibrin stabilizing factor or FSF), PK (Prekallikrein), HMWK (high-molecular-weight kininogen), tissue thromboplastin, heparin cofactor II (HCII), protein C (PC), thrombomodulin (TM), protein S (PS), von Willebrand factor (vWF) and tissue factor pathway inhibitor (TFPI), or else tissue factors.

In certain embodiments, the plasma protein consists of a coagulation protein with enzymatic activity.

The coagulation proteins with enzymatic activity encompass Factor II (prothrombin), Factor VII (proconvertin), Factor IX (anti-hemophilic Factor B), Factor X (Stuart Factor), Factor XI (Rosenthal Factor or PTA), Factor XII (Hageman Factor), Factor XIII (fibrin stabilizing factor or FSF) and PK (prekallikrein).

In certain preferred embodiments, the plasma protein consists of a natural or recombinant human plasma protein.

In preferred embodiments, the plasma protein is natural or recombinant human Factor VII.

The present invention is also illustrated, without however being limited, by the following examples.

EXAMPLES

Example 1: Obtaining an Affinity Support

Grafting buffer: 100 mM sodium acetate, pH=4.2.

Preparation of 1595 µl of aptamer at 2.5 g/l in grafting buffer, i.e. 4 mg of aptamer.

The following were respectively used for the grafting:

a) for preparing a first affinity support, an aptamer comprising the Mapt 2CS polynucleotide of sequence SEQ ID No. 1 comprising at its 5' end a hydrophilic C11 (11-amino-3,6,9-trioxaundecan-1-yl) chain;

b) for preparing a second affinity support, an aptamer comprising the "Mapt 1.2" polynucleotide of sequence SEQ ID No. 2, bonded at its 5' end to a spacer chain composed of 12 methylenes ($CH_2$) (C12 spacer) and bonded at its 3' end to an oligo-dT;

c) for preparing a third affinity support, an aptamer comprising the "Mapt 2 CS" polynucleotide of sequence SEQ ID No. 1, bonded at its 5' end to a spacer chain composed of 6 methylenes ($CH_2$) (C6 spacer).

Preparation of 1 ml of gel comprising NHS-activated carboxylic acid groups, namely the "NHS Activated Sepharose 4 fast flow (GE)" preactivated gel, by performing washing with 1 mM HCl then washing with the grafting buffer.

It was verified that the pH in the preparation of aptamer in the buffer solution was 4.2.

The aptamer preparation was mixed with 1 ml of preactivated gel. The preactivated gel was incubated in the presence of the aptamers with stirring for 48 h (+/−2H) at 4° C.

Half a reaction volume (797 µl) of 200 mM borate buffer, pH=9, was added while stirring, then the mixture was incubated for 8 h with stirring at 4° C.

The supernatant was recovered and the amount of ungrafted aptamers was assayed.

2 ml of 0.1M Tris-HCl, pH=8.5, were added with stirring for 2 h30 at 4° C. in order to block the coupling reaction.

3 cycles of addition/stirring/elimination of the supernatant comprising: 1) 1 ml of 0.1M Tris-HCl, pH=8.5, then 2) 1 ml of 0.1M sodium acetate, 0.5M NaCl, pH=4.0, were carried out in order to obtain a ready-to-use affinity support.

For all intents and purposes, it is indicated that the "NHS Activated Sepharose 4 fast flow (GE)" gel is a crosslinked agarose gel which has NHS-activated carboxylic acid functions at its surface. The carboxylic acid functions were introduced at the surface of the gel by grafting 6-aminohexanoic acid. This preactivated agarose gel is described in technical instruction manual No. 71-5000-14 AD dated March 2011 and published by GE Healthcare. The "NHS activated Sepharose 4 Fast Flow" gel has a density of activated carboxylic acid functions ranging from 16 to 23 µmol/ml of gel.

The results show that, at the end of the coupling reaction, the supernatant of the reaction medium does not comprise a detectable amount of nucleic aptamer, i.e., under the analysis conditions used, comprises an amount of aptamer of less than 0.08 mg/ml.

It can be deduced from these results that the grafting yield is 100%, or very close to 100%.

Example 2: Use of an Affinity Support for Purifying Recombinant Human Factor VII Produced in Transgenic Rabbit Milk Gel: 1 ml grafted with Mapt 2CS-PEG(C11) prepared as described in example 1, at 4 mg/ml packed in an XK-16 column (GE).

Injection of a composition of purified recombinant human Factor FVII, produced in transgenic rabbit milk (FVII-TG): 100 or 200 or 1000 µg of FVII-TG.

The FVII-TG composition used for the injection is prepared by neutralization of the citrate initially contained in the formulation with $CaCl_2$ and modification of the formulation buffer so as to obtain: between 35 and 40 mM of NaCl and between 3.2 and 4 mM of $MgCl_2$.

Buffer used for the chromatography: 50 mM Tris/50 mM NaCl/10 mM $CaCl_2$/4 mM $MgCl_2$.

Flow rate: 0.5 ml/min

Elution buffer: 50 mM Tris, 10 mM EDTA, pH=7.4

Washing or regenerating buffer: 1M NaCl/50% propylene glycol

Sanitizing solution used between each test: 0.1 or 0.5M NaOH (1 ml)+1M NaCl/50% propylene glycol (2×1 ml).

The results are represented in FIGS. 1 to 5.

FIGS. 1 and 2 show that almost all the human factor VII is retained on the affinity support at the moment the composition to be purified is passed over the said support, regardless of the amount of Factor VII contained in the starting composition. It was estimated, for the two amounts of Factor VII to be purified (100 µg and 200 µg), that less than 10% of the Factor VII contained in the starting composition is not retained on the affinity support. FIGS. 1 and 2 also show a narrow elution peak, which illustrates the excellent chromatographic properties of the affinity support of the invention.

Figure 3:
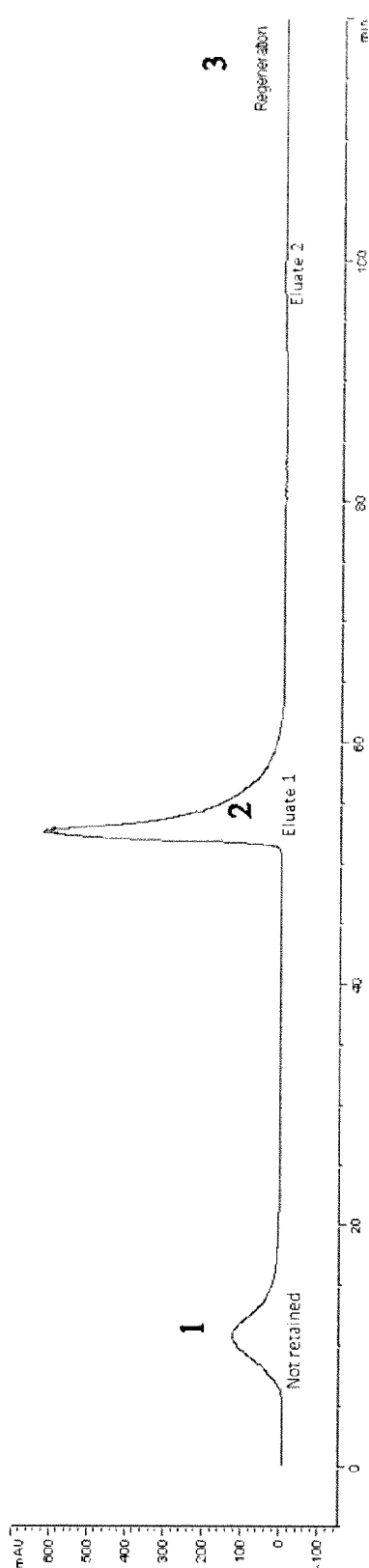
FIG. 3 shows a chromatographic profile obtained by passing a composition comprising 1000 µg of transgenic human Factor VII over a solid support of the invention onto which anti-human FVII DNA aptamers have been grafted. Peak No. 2 corresponds to the human FVII contained in the elution fraction. Peak No. 3 corresponds to the human FVII contained in the regeneration effluent. Along the x-axis: the time, expressed in minutes. Along the y-axis: the absorbance, expressed in units of Optical Density at the wavelength of 280 nanometers.

FIG. 3 shows the chromatographic profile obtained with a starting composition containing 1 mg of human Factor VII. The chromatographic profile of FIG. 3 is very similar to those represented in FIGS. 1 and 2, which illustrates the very high capacity for retention of a target ligand of the affinity support of the invention.

Figure 4:
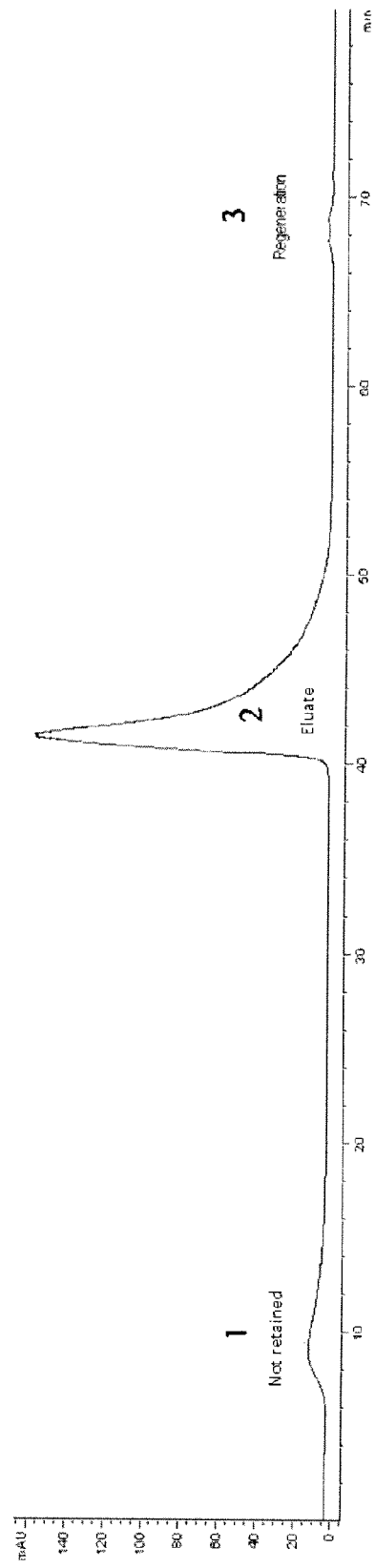
FIG. 4 shows a chromatographic profile obtained by passing a composition comprising 200 µg of transgenic human Factor VII over a solid support of the invention onto which anti-human FVII DNA aptamers have been grafted, said support having been subjected beforehand to a treatment with a sanitizing solution comprising 0.5 M of NaOH. Peak No. 2 corresponds to the human FVII contained in the elution fraction. Peak No. 3 corresponds to the human FVII contained in the regeneration effluent. Along the x-axis: the time, expressed in minutes. Along the y-axis: the absorbance, expressed in units of Optical Density at the wavelength of 280 nanometers.
Figures 5, 6:
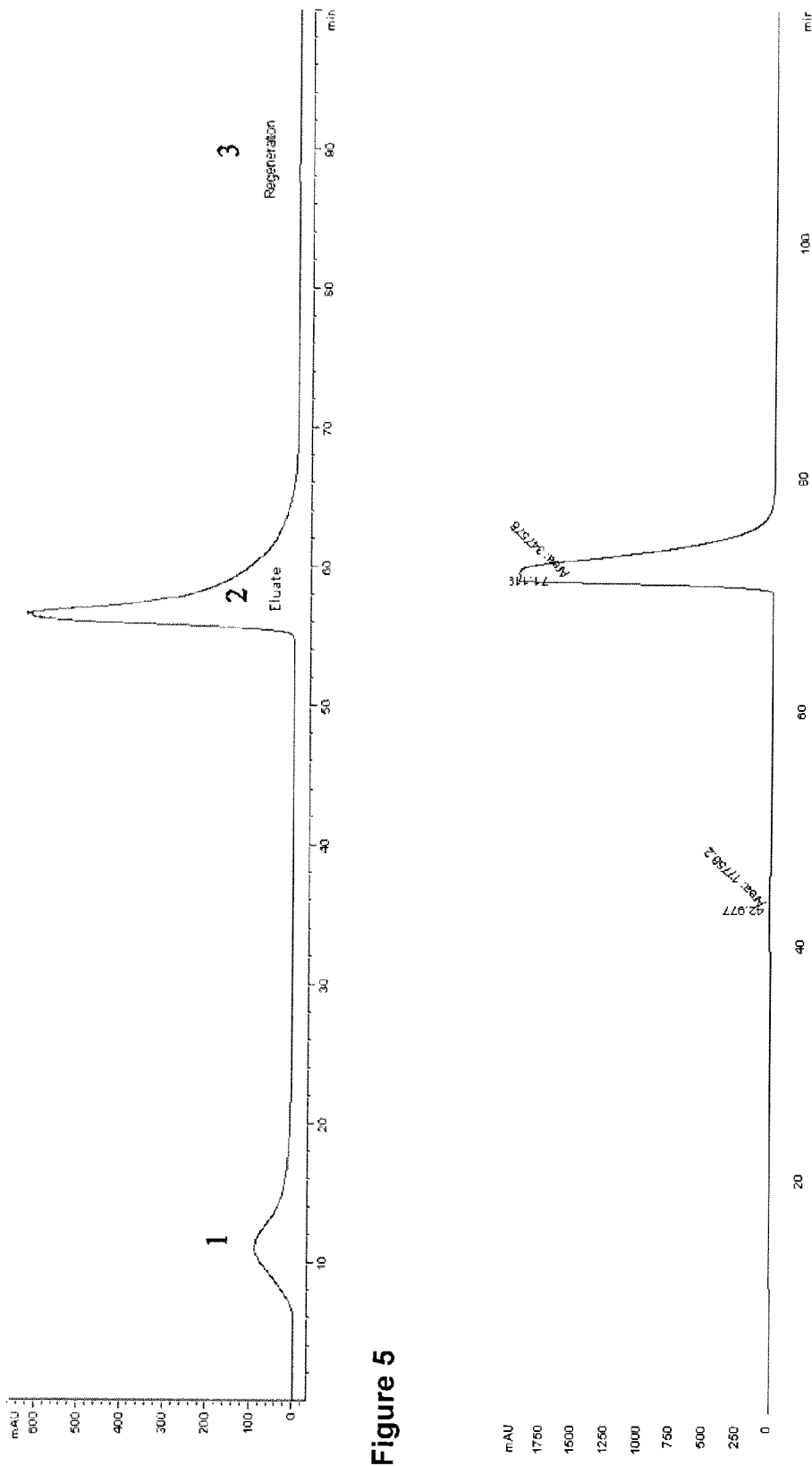
FIG. 5 shows a chromatographic profile obtained by passing a composition comprising 1000 µg of transgenic human Factor VII over a solid support of the invention onto which anti-human FVII DNA aptamers have been grafted, said support having been subjected beforehand to a treatment with a sanitizing solution comprising 0.5 M of NaOH. Peak No. 2 corresponds to the human FVII contained in the elution fraction. Peak No. 3 corresponds to the human FVII contained in the regeneration effluent. Along the x-axis: the time, expressed in minutes. Along the y-axis: the absorbance, expressed in units of Optical Density at the wavelength of 280 nanometers.
FIG. 6 shows a chromatographic profile obtained by passing a composition comprising 2.7 mg of transgenic human Factor VII over a solid support of the invention onto which anti-human FVII DNA aptamers have been grafted under the following coupling conditions: 48 h, 5° C., pH 4.2. Point No. 1 (at approximately 45 min) indicates the moment of the injection of human factor VII. Peak No. 2 (at approximately 70 min) corresponds to the human FVII contained in the elution fraction. Along the x-axis: the time, expressed in minutes. Along the y-axis: the absorbance, expressed in units of Optical Density at the wavelength of 280 nanometers.
Figure 7:
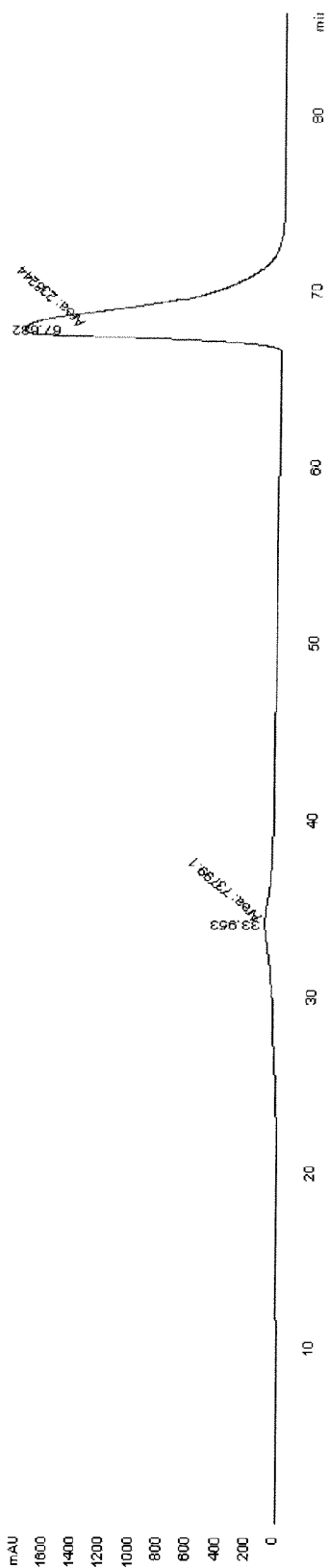
FIG. 7 shows a chromatographic profile obtained by passing a composition comprising 2.7 mg of transgenic human Factor VII over a solid support of the invention onto which anti-human FVII DNA aptamers have been grafted under the following coupling conditions: 48 h, 5° C., pH 3.8. Point No. 1 (at approximately 35 min) indicates the moment of the injection of human Factor VII. Peak No. 2 (at approximately 70 min) corresponds to the human FVII contained in the elution fraction. Along the x-axis: the time, expressed in minutes. Along the y-axis: the absorbance, expressed in units of Optical Density at the wavelength of 280 nanometers.
Figure 8:
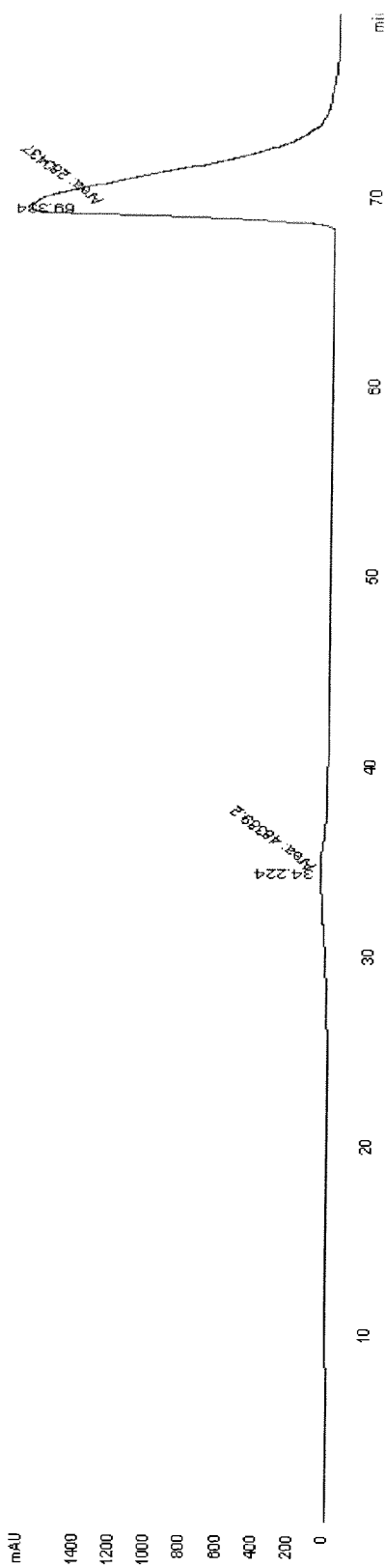
FIG. 8 shows a chromatographic profile obtained by passing a composition comprising 2.7 mg of transgenic human Factor VII over a solid support of the invention onto which anti-human FVII DNA aptamers have been grafted under the following coupling conditions: 2 h, 5° C., pH 4.2. Point No. 1 (at approximately 35 min) indicates the moment of the injection of human Factor VII. Peak No. 2 (at approximately 70 min) corresponds to the human FVII contained in the elution fraction. Along the x-axis: the time, expressed in minutes. Along the y-axis: the absorbance, expressed in units of Optical Density at the wavelength of 280 nanometers.
Figure 9:
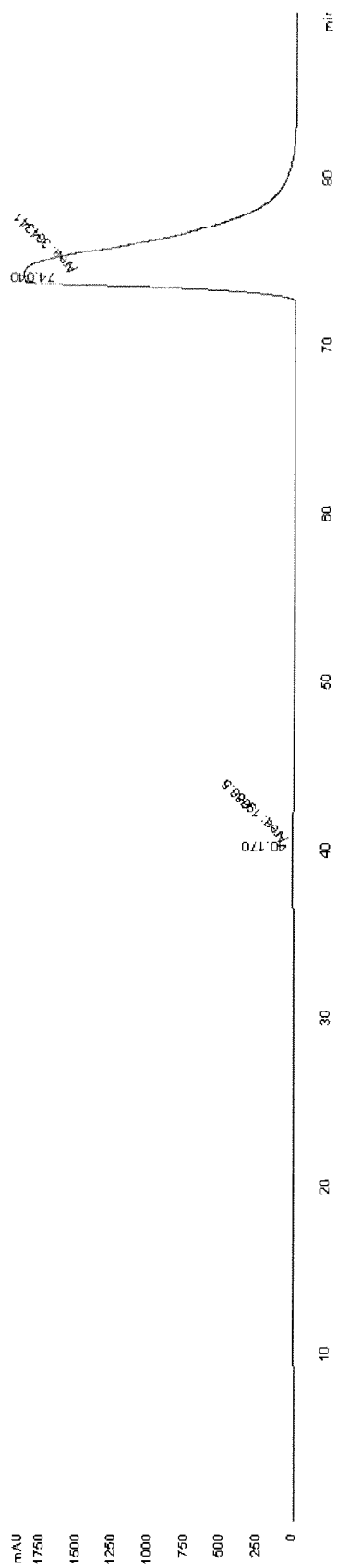
FIG. 9 shows a chromatographic profile obtained by passing a composition comprising 2.7 mg of transgenic human Factor VII over a solid support of the invention onto which anti-human FVII DNA aptamers have been grafted under the following coupling conditions: 1 h, RT (room temperature), pH 4.2. Point No. 1 (at approximately 40 min) indicates the moment of the injection of human Factor VII. Peak No. 2 (at approximately 75 min) corresponds to the human FVII contained in the elution fraction. Along the x-axis: the time, expressed in minutes. Along the y-axis: the absorbance, expressed in units of Optical Density at the wavelength of 280 nanometers.

FIGS. 4 and 5 show the chromatographic profiles obtained by purification of an amount of human Factor VII of 200 µg (FIG. 4) and 1000 µg (FIG. 5) on an affinity support prepared as described in example 1 and having undergone drastic sanitizing treatment steps with a sanitizing solution comprising a mixture of 0.5M NaOH and 50% of propylene glycol. The chromatographic profiles obtained show the capacity of an affinity support according to the invention to withstand deleterious sanitizing treatments.

It is specified that the same chromatographic profile is obtained when a succession of transgenic human Factor VII purifications and washing and sanitizing steps is carried out. This demonstrates the excellent stability of the affinity support, which makes it possible to purify target ligands of interest extremely reproducibly.

Example 3: Grafting Yield as a Function of the Amount of Aptamers Used and Loading Capacity of the Affinity Supports Obtained The influence of the amount of aptamers on the grafting yield and the loading capacity of the affinity supports was studied for the Mapt 2CS-(hydrophilic C11) and Mapt 2.2CS-(hydrophilic C11) aptamers. The rafting protocol used is identical to that described in example 1. The Mapt 2.2CS-(hydrophilic C11) aptamer is a result of the coupling of Mapt 2.2CS of sequence SEQ ID No. 3 and of 11-(trifluoroacetamido)-3,6,9-trioxaundecan-1-yl [(2-cyanoethyl)(N,N-diisopropyl)]phosphoramidite (Link Technologies), followed by the generation of the phosphodiester group by oxidation and elimination of the cyanoethyl group and by the subsequent deprotection of the primary amine function present at the end of the spacer chain. Mapt 2.2CS is directed against factor VII.

The loading capacity (or in other words the retention capacity) of the affinity supports, expressed in mg of FVII per ml of gel, was evaluated by injection of a composition of recombinant human FVII in "Tp5" buffer (50 mM Tris, 10 mM $CaCl_2$, pH 7.5).

Tables 1 and 2 below give the yield of the reaction for grafting the Mapt 2CS-PEG(C11) and Mapt 2.2CS-PEG (C11) aptamers onto the "NHS Activated Sepharose 4 fast flow (GE)" preactivated gel as a function of the amount of aptamers used in the reaction per ml of gel. The yield was determined by quantification of the amount of aptamers present in the supernatant at the end of the coupling reaction by quantitative PCR.

The final amount of aptamers grafted per ml of gel is also indicated in tables 1 and 2 below.

TABLE 1

Influence of the amount of Mapt 2CS aptamer per ml of gel on the yield of the coupling reaction and the features of the affinity support obtained

| Amount of aptamers used in mg/ml of gel | Yield of the coupling reaction | Amount of aptamers grafted in mg/ml of gel | Amount of aptamers grafted in µmol/ml of gel | Percentage of carboxylic acid sites of the gel coupled to an aptamer |
|---|---|---|---|---|
| 0.1 | 99.97% | 0.1 | 0.007 | 0.04% |
| 0.2 | 99.96% | 0.2 | 0.014 | 0.07% |
| 0.6 | 99.95% | 0.6 | 0.042 | 0.21% |
| 0.8 | 99.94% | 0.8 | 0.056 | 0.29% |
| 1.0 | 100% | 1.0 | 0.07 | 0.36% |
| 2.0 | 100% | 2.0 | 0.12 | 0.6% |
| 3.5 | 100% | 3.5 | 0.23 | 1.2% |
| 6.0 | 97% | 5.8 | 0.39 | 2% |

TABLE 2

Influence of the amount of Mapt 2.2CS aptamer per ml of gel on the yield of the coupling reaction and the features of the affinity support obtained

| Amount of aptamers used in mg/ml of gel | Yield of the coupling reaction | Amount of aptamers grafted in mg/ml of gel | Amount of aptamers grafted in µmol/ml of gel | Percentage of carboxylic acid sites of the gel coupled to an aptamer |
|---|---|---|---|---|
| 0.1 | 100% | 0.1 | 0.007 | 0.04% |
| 3.5 | 100% | 3.5 | 0.23 | 1.2% |
| 6.0 | 92.6% | 5.55 | 0.37 | 1.9% |

The coupling yields obtained for the Mapt 2.2CS-PEG (C11) and Mapt 2CS-PEG(C11) aptamers are between 90% and 100% for all the amounts of aptamers tested. Notably, it is possible to graft up to 0.4 µmol per ml of gel, which corresponds to a percentage functionalization of the activated carboxylic acid functions present at the surface of the gel of 2%.

The loading capacity of the affinity supports for recombinant human FVII varies in a linear fashion with the amount of aptamers grafted per ml of gel. No effect of saturation of the loading capacity of the support and therefore of loss of functionality of the aptamers is thus observed for the high amounts of aptamers grafted.

In view of these results, it could be possible to obtain affinity supports which have a grafted aptamer density of greater than 6 mg/ml and which have a loading capacity for FVII greater than 8 mg of recombinant human FVII per ml of gel.

Table 3 below gives the loading capacity of the affinity supports as a function of the number of aptamers grafted at their surface.

TABLE 3

Loading capacity of the affinity supports obtained

|  | Mapt 2CS-PEG(C11) | | | | Mapt 2.2CS-PEG(C11) | | |
|---|---|---|---|---|---|---|---|
| Amount of aptamers grafted in mg/ml of gel | 0.1 | 1.00 | 3.50 | 5.80 | 1.00 | 3.50 | 5.60 |
| Amount of aptamers grafted in µmol/ml of gel | 0.007 | 0.07 | 0.23 | 0.39 | 0.07 | 0.23 | 0.37 |
| Human FVII loading capacity, expressed in mg of FVII/ml of gel | 0.05 | 1.00 | 3.60 | 5.40 | 1.6 | 5.2 | 8.0 |

Example 4: Comparative Tests of Chemical Grafting of Nucleic Acids onto a Solid Support Preactivated with NHS Groups 4.1. Comparative Tests Using Various pH Conditions Comparative tests of grafting of the starting preactivated support used in example 1, under neutral or slightly alkaline pH conditions, were carried out as described in table 4 given hereinafter:

TABLE 4

| Mapt 2CS | Modification (nature of the spacer) | Test | Amount of aptamer | Conditions: Grafting buffer |
|---|---|---|---|---|
| Oligo 1 | 5' amine | Test 1 | 6.5 mg | 100 mM MOPS, 10 mM |
| Oligo 1 | C6 spacer | Test 2 | 6.5 mg | CaCl$_2$, pH 7.0 (Condition 1) |
| Oligo 1 |  | Test 3 | 6.5 mg | 100 mM MOPS, 10 mM CaCl$_2$, 0.5M NaCl, pH 7.0 (Condition 2) |
| Oligo 4 | 5' amine C12 spacer 3'dT | Test 4 | 3.5 mg | 0.2M NaHCO$_3$, 0.5M NaCl, pH 8.3 (Condition 3) |
|  |  | Test 5 | 3.5 mg | 0.2M NaHCO$_3$, 2M NaCl, pH 8.3 (Condition 4) |
| Oligo 5 | 5' amine hydrophilic C11 spacer | Test 5 | 6.5 mg | 100 mM MOPS, 10 mM CaCl$_2$, 0.5M NaCl, pH 7.0 (Condition 2) |

The following protocol was used:
1 ml of gel rinsed with 15 ml of 1 mM HCl and then 7 ml of grafting buffer. Addition of the 6.5 ml (or 3.5 ml) of Mapt 2CS at 1 g/l and incubation of the gel with Mapt 2CS for 4 hours at room temperature.
Neutralization of the activated sites with a 50 mM Tris buffer, pH=7.4.

The amount of aptamers not grafted at the output of the column after the gaffing step was measured. The results show that the grafting yield ranges from 0% to a maximum of 10%, regardless of the grafting conditions described in table 1 that were used. Contrary to what was observed by Goss et al. (above), a high salinity is not sufficient to increase the coupling yield.

4.2. Comparative Tests while Neutralizing the Negative Charges of the Nucleic Acids to be Grafted by Adding Divalent Cations or by Adding NaCl The following protocol was used:
100 µl of gel rinsed with 15 ml of 1 mM HCl then 700 µl of grafting buffer/addition of the 650 µl of Mapt 2CS (oligo 5) at 130 mg/l and incubation of the gel with Mapt 2CS for 4 hours at room temperature.
Conditions used:
Condition 1: 92 mM MOPS buffer, pH=7.0, 200 mM CaCl$_2$, 200 mM MgCl$_2$
Condition 2: 92 mM MOPS buffer, pH=7.0, 200 mM CaCl$_2$, 200 mM MgCl$_2$
Condition 3: 0.2M NaHCO$_3$, 0.5M NaCl, pH 8.3
Condition 4: 0.2M NaHCO$_3$, 2M NaCl, pH 8.3.

The amount of nongrafted aptamer at the column output after the grafting step was measured. The results show that the grafting yield, whatever the grafting conditions described above, ranges from 0% to a maximum of 10%.

The result of all the experiments presented above is that carrying out the coupling step in the presence of a basic or neutral pH as recommended in the prior art or in the instruction leaflets of the preactivated gels gives a coupling yield for the aptamers on the preactivated gel which is very low, i.e. less than 10%.

Increasing the ionic strength through the use of a solution of NaCl at a concentration ranging up to 2M, or using divalent cation salts capable of masking the negative charges of the aptamers, does not make it possible to increase the coupling yield.

Contrary to what those skilled in the art could have expected, carrying out the coupling step in the presence of an acid pH makes it possible to significantly increase the coupling of the aptamers on the preactivated support without harming the capacity of said aptamers to bind to their target protein.

Example 5: Modulation of the Parameters for Carrying Out the Coupling Reaction According to the Present Invention The influence of the pH, of the temperature and of the duration of the reaction were evaluated in order to determine the parameters controlling the reaction for coupling of the activated carboxylic acid functions of the gel ("NHS-activated Sepharose 4 fast Flow") with the aliphatic primary amine functions present on the spacer chains of the Mapt 2CS-PEG (C11) aptamers.

The following protocol was followed:
The grafting buffer was prepared using 100 mM sodium acetate with adjustment to the desired pH, except when the reaction was carried out at a pH=8.3, in which case an NaHCO$_3$ buffer was prepared.
A solution of Mapt 2CS-PEG (C11) aptamers at a concentration of 2 g/l in the grafting buffer was prepared.
1 ml of the aptamer solution was mixed with 1 ml of gel and incubated at the desired temperature, with stirring.

The progression of the coupling reaction is monitored by quantification of the aptamers present in the supernatant.

At the end of the kinetic monitoring of the reaction, 1 ml of 200 mM borate buffer at pH 9 was added to the reaction medium, with stirring, and then the resulting mixture was incubated for 3 h with stirring at 4° C. The supernatant was removed for the final assaying thereof. The neutralization of the residual carboxylic acid functions of the gel was carried out by adding 2 ml of Tris-HCl buffer at 0.1M and at pH=8.5 with stirring for 2 h30 at 4° C.

3 cycles of addition/stirring/removal of the supernatant comprising: 1) 1 ml of Tris-HCl at 0.1M, pH=8.5, then 2) 1 ml of sodium acetate at 0.1M, 0.5M NaCl, pH=4.0, were carried out.

The supernatant was removed. The resulting gel is stored in Tp1 buffer supplemented with 0.2% azide for storage at 4° C.

The results of the kinetic monitoring of the coupling reaction as a function of the temperature, the duration of the reaction and the pH are given in table 5 hereinafter:

TABLE 5

Influence of the reaction temperature (RT: room temperature), of the pH and of the duration of the reaction

| | pH | T° C. | Duration | Reaction yield (%) |
|---|---|---|---|---|
| Influence of the pH | 3.8 | 5° C. | 48 h | 99.8 |
| | 4.3 | 5° C. | 48 h | 98.4 |
| | 4.8 | 5° C. | 48 h | 75.9 |
| | 5.6 | 5° C. | 48 h | 64.9 |
| | 8.3 | 5° C. | 48 h | 10 |
| Influence of the temperature and of the duration of the reaction | 4.3 | 5° C. | 24 h | 99.5 |
| | 4.3 | 5° C. | 2 h | 100 |
| | 4.3 | 5° C. | 4 h | 100 |
| | 4.3 | 5° C. | 6 h | 100 |
| | 4.3 | 5° C. | 8 h | 100 |
| | 4.3 | 5° C. | 24 h | 100 |
| | 4.3 | 5° C. | 48 h | 97.8 |
| | 4.3 | RT* | 1 h | 100 |
| | 4.3 | RT* | 2 h | 100 |
| | 4.3 | RT* | 3 h | 100 |
| | 4.3 | RT* | 3 h | 99.8 |

As is illustrated in table 5 above, the pH is a crucial parameter for carrying out the coupling reaction according to the invention.

Carrying out the reaction according to the conditions described in the prior art, i.e. at a basic pH of 8.3, gives a very low coupling yield of at most 10%. Reducing the pH makes it possible to significantly improve the reaction yield. A yield of at least 98% is in particular observed for a pH of approximately 18 to 4.3. Such a result is entirely surprising: those skilled in the art would expect a low coupling yield at these pHs owing to the degradation of the nucleic acids by acid hydrolysis and to the decrease in the reactivity of the primary amines. In view of these experimental results, it appears that the coupling reaction can be carried out without distinction at low temperature or at room temperature.

Notably, the affinity supports obtained at pH=3.8 or at room temperature at pH=4.3 have a recombinant human Factor VII loading capacity (i.e. retention capacity) equivalent to the supports obtained at pH=4.2 and at 5° C. Generally, the loading capacities obtained are particularly high, which reflects not only a high degree of grafting of the aptamers, but also the maintaining of the capacity of the aptamers to bind specifically to their target protein. In other words, carrying out the coupling reaction between the activated carboxylic acid functions of the support and the primary amine functions present on the spacer of the aptamers, at room temperature and at a pH of less than 4.5, makes it possible not only to obtain a grafting yield close to 100%, but also to maintain the functional integrity of the aptamers.

Example 6: Additional Embodiments of an Affinity Support

Other affinity supports were prepared by varying (i) the grafting conditions and also (ii) the types of aptamers used.

6.1. Types of Aptamers Grafted

With regard to the types of aptamers, aptamers comprising a DNA polynucleotide and aptamers comprising an RNA polynucleotide were respectively used. Furthermore, for certain aptamers, the polynucleotide is bonded to a spacer chain via its 5' end, while for the other aptamers, the polynucleotide is bonded to a spacer chain via its 3' end. Likewise, aptamers comprising a hydrophilic spacer chain or a hydrophobic spacer chain were used.

The aptamers used in example 6 are the following:

the aptamer comprising the "Mapt 2CS" DNA polynucleotide of sequence SEQ ID No. 1 comprising at its 5' end the hydrophilic C11 spacer chain described for the preparation of the first affinity support disclosed in paragraph "a)" of example 1, said aptamer being denoted "Mapt 2CS oligo5 (5' Amine hydrophilic C11)" in table 6;

the aptamer comprising the "Mapt 2CS" DNA polynucleotide of sequence SEQ ID No. 1 comprising at its 5' end the hydrophobic C6 spacer chain described for the preparation of the third affinity support disclosed in paragraph "c)" of example 1 and comprising at its 3' end an inverted deoxyribothymidine residue (3'-dT-5'), said aptamer being denoted "Mapt 2CS oligo2 (5' Amine C6 and 3' dT) in table 6;

the aptamer comprising the "Mapt 2CS" DNA polynucleotide of sequence SEQ ID No. 1 comprising at its 5' end the hydrophobic C12 spacer chain described for the preparation of the second affinity support disclosed in paragraph "b)" of example 1, said aptamer being denoted "Mapt 2CS oligo3 (5' Amine C12)" in table 6;

the aptamer comprising the "Mapt 2CS" DNA polynucleotide of sequence SEQ ID No. 1 comprising at its 3' end the hydrophobic C6 spacer chain described for the preparation of the third affinity support disclosed in paragraph "c)" of example 1, said aptamer being denoted "Mapt 2CS oligo7 (3' Amine C6)" in table 6;

the aptamer comprising the "Mapt anti-FIXa RNA" RNA polynucleotide of sequence SEQ ID No. 4 comprising at its 5' end the hydrophilic C11 spacer chain described for the preparation of the first affinity support disclosed in paragraph "a)" of example 1 and comprising at its 3' end an inverted deoxyribothymidine residue (3'-dT-S'), said aptamer being denoted "Mapt anti-FIXa RNA 5' Amine hydrophilic C11" in table 6.

An affinity support onto which was grafted an aptamer comprising the "Mapt 1.2CSO" DNA polynucleotide of sequence SEQ ID No. 5 comprising at its 5' end the hydrophilic C11 spacer chain described for the preparation of the first affinity support disclosed in paragraph "a)" of example 1 was also prepared, said aptamer being denoted "Mapt 1.2CSO oligo5 (5' Amine hydrophilic C11)". The results regarding the latter aptamer are not given in table 6 which follows.

6.2. RNA Aptamer Grafting Conditions

The RNA aptamer of sequence SEQ ID No. 5 was grafted under the following conditions:

300 µg of RNA aptamer were incubated with 500 µl of gel, at the final gel concentration of 0.6 g/l;

the grafting reaction was carried out for 2.5 hours at 17° C. (RT) and at pH 4.2;

the reaction was then stopped by neutralization with a 200 mM borate buffer for 2.5 hours at 17° C. and at pH 9;

the residual amount of nongrafted aptamers in the supernatant was measured in order to determine the grafting yield, by agarose gel electrophoresis and staining with GelRed® (at 3.5%), followed by comparison with a calibration range of known amounts of the RNA aptamer loaded onto other lanes of the same electrophoresis gel.

The results show that the grafting yield was greater than 99%. These results show that the grafting process at a pH of less than 5 is efficient for the grafting of all types of nucleic ligands, whether these nucleic ligands comprise a DNA polynucleotide or an RNA polynucleotide (and therefore also nucleic ligands comprising a DNA/RNA hybrid polynucleotide), including ligands comprising a polynucleotide with modified bases, including an RNA polynucleotide with modified bases.

6.3. Efficiency of the Grafting Reaction

The coupling reaction was carried out as described in example 5, except for specific indication regarding the duration, the temperature and the pH. The results are given in table 6 hereinafter.

TABLE 6

| Aptamer | Grafting conditions* (duration; temp; pH) | Degree of grafting targeted (mg/ml of gel)** | Grafting yield (%)** |
|---|---|---|---|
| Mapt 2CS oligo5 (5' Amine hydrophilic C11) | 48 h; 5° C.; pH 4.3 | 4.4 | ≈100 |
| | 48 h; 5° C.; pH 3.8 | 4.4 | ≈100 |
| | 2 h; 5° C.; pH 4.3 | 4.4 | ≈100 |
| | 1 h; RT; pH 4.3 | 4.4 | ≈100 |
| | 2 h; 5° C.; no pH neutralization | 4.4 | ≈100 |
| Mapt 2CS oligo2 (5' Amine C6 and 3' dT) | 2 h; RT; pH 4.3 | 0.7 | ≈100 |
| Mapt 2CS oligo3 (5' Amine C12) | 2 h; RT; pH 4.3 | 0.7 | ≈100 |
| Mapt 2CS oligo7 (3' Amine C6) | 2 h; RT; pH 4.3 | 0.8 | ≈100 |
| Mapt 1.2CSO oligo5 (5' Amine hydrophilic C11) | 2 h; 5° C.; pH 4.3 | ND*** | ≈100 |
| Mapt anti-FIXa RNA 5' Amine hydrophilic C11 and 3'dT5' | 2 h; RT; pH 4.2 | 0.6 | ≈100 |

*Duration of the coupling reaction expressed in hours; temperature expressed in degrees Celsius - RT = room temperature (18° C.-25° C.)
**The degree of grafting targeted is achieved for a grafting yield of 100%. The grafting yield was measured as described in example 3
***ND = not determined The results of table 6 show that, for a given aptamer, a grafting yield of 100% is obtained whatever the conditions tested.

In particular, these results confirm those of example 4, and more specifically the results of table 5, which show that a maximum grafting yield is obtained, even at the very acidic pH of 3.8. These results also confirm the rapid kinetics of the coupling reaction carried out at room temperature.

It is also shown that the neutralization step at pH 9, subsequent to the coupling reaction, is not essential for obtaining a maximum grafting yield, since the degree of grafting and the grafting yield under these conditions are identical to those observed when the neutralization step is carried out (see table 6 above).

The results of table 6 also show that the hydrophilic or hydrophobic nature of the spacer chain of the aptamer has no influence on the grafting efficiency. It is also shown that the grafting is also efficient when the hydrophilic or hydrophobic spacer chain is bonded to the 5' end or to the 3' end of the DNA or RNA polynucleotide.

It is added that the prior neutralization of the charges of the DNA polynucleotide by incubation thereof with a Polybrene® (hexamethrine bromide, 1,5-dimethyl-1,5-diazaundecamethylene polymethobromide) makes it impossible to carry out the coupling reaction.

6.4. Functionality of the Affinity Supports

The functionality of affinity supports on which the "Mapt 2CS oligo5" aptamer described in section 6.1. above was immobilized was tested respectively under the following coupling reaction temperature, duration and pH conditions:

Conditions No. 1: 48 h, 5° C., pH 4.2;
Conditions No. 2: 48 h, 5° C., pH 3.8;
Conditions No. 3: 2 h, 5° C., pH 4.2; and
Conditions No. 4: 1 h, RT (room temperature), pH 4.2.

500 µl of gel grafted with the aptamers under each of the conditions No. 1 to 4 above, at the final concentration of 4.4 mg/ml, were used for the test.

For each of the chromatography supports, 2.7 mg of a composition of purified recombinant human FVII, produced in transgenic rabbit milk (FVII-TG), were injected.

The FVII-TG composition used for the injection is prepared by neutralization of the citrate initially contained in the formulation with $CaCl_2$ and modification of the formulation buffer so as to obtain: between 35 and 40 mM of NaCl and between 3.2 and 4 mM of $MgCl_2$.

Buffer used for the chromatography: 50 mM Tris/10 mM $CaCl_2$, pH 7.5

Flow rate: 0.5 ml/min

Elution buffer: 50 mM Tris, 10 mM EDTA, pH=7.5.

The results are represented in FIGS. 6 to 9, respectively for the coupling conditions No. 1 to 4 described above. The results are also represented in table 7 below.

TABLE 7

| Coupling conditions (duration; temperature; pH) | FVII fraction not retained on the column (%) | FVII fraction eluted (%) |
|---|---|---|
| No. 1: 48 h; 5° C.; pH 4.2 | 5 | 95 |
| No. 2: 48 h; 5° C.; pH 3.8 | 24 | 76 |
| No. 3: 2 h; 5° C.; pH 4.2 | 15 | 85 |
| No. 4: 1 h; RT; pH 4.2 | 5 | 95 |

The results of FIGS. 6 to 9 and of table 7 above show that almost all the human factor VII is retained on the affinity support at the time the composition to be purified is passed over said support, with the exception of the affinity support prepared by grafting according to conditions No. 2 (48 h, 5° C., pH 3.8), for which a degree of retention of the factor VII which is substantial but not the maximum is observed.

The results also show that all of the human factor VII retained on the affinity support is released during the elution step.

These results show that completely functional affinity supports can be prepared by using the grafting conditions No. 1 and No. 3-4, which means that the grafting temperature and duration conditions are not absolutely determining from the viewpoint of the capacity of the affinity support obtained to retain and then release the target molecule.

In particular, it is observed that the conditions for coupling the aptamers for a short period of time (1 hour) and at high temperature (room temperature) (i) enable a 100% degree of grafting of the aptamers and (ii) do not lead to any impairment of the capacity of the grafted aptamers to bind to the target human factor VII.

On the other hand, the poorer results obtained with the affinity support prepared by coupling the aptamers at pH 3.8 show that the pH conditions are important for maintaining the integrity of the grafted aptamers, and in particular for maintaining the ability of the grafted aptamers to bind to the target human factor VII. When the coupling reaction is carried out at pH 3.8, an affinity support is obtained which remains functional for selectively enriching a starting sample with human factor VII. However, such an affinity support cannot be validly used in the context of an industrial process for purifying human factor VII, owing to the considerable loss of factor VII (more than 20%) and therefore to the economically unfavorable nature of such a process.

Example 7: Maintaining the Integrity of the Affinity Support Under Conditions of Industrial Use Involving Contacts in Biological Media and a Powerful Sanitizing Step (Sodium Hydroxide at a Concentration of 1M)

In example 7, it is shown that affinity supports as defined in the present description preserve their capacity for retaining and eluting the target protein, even after numerous cycles of use, under industrial processing conditions.

7.1. Preparation of the Grafting Supports

Three grafting supports were prepared as described in example 1, using, respectively, each of the following three aptamers:

grafting support No. 1: an aptamer comprising the Mapt 2CS polynucleotide of sequence SEQ ID No. 1 comprising at its 5' end a hydrophilic C11 (11-amino-3,6,9-trioxaundecan-1-yl) chain, grafting support No. 2: an aptamer comprising the Mapt 2.2CS polynucleotide of sequence SEQ ID No. 3 comprising at its 5' end a hydrophilic C11 (11-amino-3,6,9-trioxaundecan-1-yl) chain, and grafting support No. 3: an aptamer comprising the "Mapt 2.2CS" polynucleotide of sequence SEQ ID No. 3 bonded at its 5' end to a spacer chain composed of 6 methylenes ($CH_2$) (C6 spacer).

The grafting yields were, respectively, 100% (grafting support No. 1), 93% (grafting support No. 2) and 87% (grafting support No. 3).

The theoretical static capacity of the affinity supports prepared, i.e. the amount of human FVII which should be retained on the affinity supports if each of the grafted aptamers bound a human FVII molecule, was, respectively, 18.7 mg per milliliter of support (support No. 1), 17.3 mg/ml (support No. 2) and 16.3 mg/ml (support No. 3).

7.2. Operating Conditions of the Process for Purifying Human FVII

An FVII-TG composition enriched with human FVII was used, the final FVII-TG concentration being approximately 50 000 ppm, said composition comprising a large proportion of des-gla forms of FVII (inactive forms of FVII) and said composition having an FVII specific activity of approximately 0.4 (activity expressed as amidolytic activity/antigen).

The general protocol is the following:

equilibration of the support in TP4 buffer (50 mM Tris, 10 mM $CaCl_2$, 4 mM $MgCl_2$, pH 7.5), using a buffer volume which is five times the volume of the grafted support, injection of the raw material (FVII-TG composition), dialyzed beforehand against a 50 mM Tris buffer containing 10 mM $CaCl_2$ and 4 mM $MgCl_2$, washing with the washing buffer (eight times the volume of the grafted support), and equilibration with a 50 mM Tris, 10 mM EDTA equilibration buffer at pH 7.5 (three times the volume of the grafted support).

7.3. Properties of the Supports for Purifying Human FVII

The capacity of the three supports prepared as described in section 7.1. above to selectively retain active human FVIIa was tested.

It was determined that the three supports had a dynamic capacity for retention of human FVIIa of approximately 10 mg of human FVIIa per milliliter of grafted support, which represents between 53% and 58% of the theoretical maximum static capacity calculated in section 7.1. above. These results show that the respective aptamers grafted onto the three supports are greatly accessible and functional.

It was also shown that each of the three affinity supports prepared as described in section 7.1. above was capable of selectively retaining human FVII molecules having an active GLA domain, as is described in table 8 below.

TABLE 8

|  | Affinity support No. 1 | Affinity support No. 2 | Affinity support No. 3 |
| --- | --- | --- | --- |
| Start |  |  |  |
| FVII (OD280) mg | 17 | 17 | 15 |
| FVIIam IU | 13906 | 139060 | 12270 |
| FVIIam/FVII:Ag ratio | 0.41 | 0.41 | 0.41 |
| Not retained |  |  |  |
| FVII (OD280) mg | 7.7 | 9.7 | 7.8 |
| FVIIam IU | 94 | 273 | 134 |
| FVIIam/FVII:Ag ratio | 0.006 | 0.014 | 0.009 |
| FVII yield (OD) % | 45.5 | 56.9 | 52.1 |
| FVIIam yield % | 0.7 | 2.0 | 1.1 |
| Eluate |  |  |  |
| FVII (OD280) mg | 7.7 | 7.3 | 6.3 |
| FVIIam IU | 12270 | 10675 | 9055 |
| FVIIam/FVII:Ag ratio | 0.80 | 0.71 | 0.72 |
| FVII yield (OD) % | 45.3 | 42.9 | 42.0 |
| FVIIam yield % | 88.2 | 76.8 | 73.8 |

The results of table 8 show that, from a composition comprising only 41% of human FVII comprising an active GLA domain, relative to the total amount of human FVII present in said composition, a final composition enriched with human FVII, which comprises from 70% to 80% of human FVII comprising an active GLA domain, relative to the total amount of human FVII present in said enriched composition, is obtained. These results show that the three affinity supports (i) make it possible to purify human FVII and (ii) make it possible to obtain a composition of purified FVII which is enriched in active form of human FVII, by removing the inactive forms of human FVII.

7.4. Resistance of the Affinity Supports with Respect to a Sodium Hydroxide Treatment The resistance of the three affinity supports to a prolonged treatment with a 1M sodium hydroxide solution was tested.

The supports prepared as described in section 7.1. were brought into contact with a 1M sodium hydroxide solution for a period of 100 hours. After washing in order to remove the sodium hydroxide, the capacity of each of the three affinity supports to purify human FVII was measured. The results are given in table 9 below.

TABLE 9

|  | Affinity support No. 1 | Affinity support No. 2 | Affinity support No. 3 |
|---|---|---|---|
| Start |  |  |  |
| FVII (OD280) mg | 17 | 17 | 15 |
| FVIIam IU | 13906 | 13906 | 12270 |
| FVIIam/FVII:Ag ratio | 0.41 | 0.41 | 0.41 |
| Not retained |  |  |  |
| FVII (OD280) mg | 8.1 | 9.2 | 7.9 |
| FVIIam IU | 156 | 434 | 163 |
| FVIIam/FVII:Ag ratio | 0.010 | 0.024 | 0.010 |
| FVII yield (OD) % | 47.7 | 53.9 | 52.5 |
| FVIIam yield % | 1.1 | 3.1 | 1.3 |
| Eluate |  |  |  |
| FVII (OD280) mg | 7.9 | 7.1 | 6.9 |
| FVIIam IU | 13560 | 11500 | 12215 |
| FVIIam/FVII:Ag ratio | 0.9 | 0.82 | 0.89 |
| FVII yield (OD) % | 46.5 | 41.5 | 45.7 |
| FVIIam yield % | 97.5 | 82.7 | 99.6 |

The results of table 9 show that treatment with 1M sodium hydroxide for a very long period of time (100 hours) does not cause any significant change in the capacity of supports No. 1, No. 2 and No. 3 to purify human FVII.

7.5. Resistance of the Affinity Supports with Resect to Prolonged Contact with Various Biological Media The resistance of the three affinity supports to prolonged treatment with various biological media, which can be used as starting products in processes for purifying human FVII, was tested. The following two biological media were in particular tested: (i) a cryosupernatant of human blood plasma and (ii) a clarified milk solution, it being possible for milk to constitute a source of human FVII, for example when the human FVII is produced in the milk of animals which are transgenic for the gene encoding human FVII.

Affinity support No. 1 prepared as described in section 7.1. was brought into contact with (i) a human plasma cryosupernatant or (ii) a clarified milk, for a period of 100 hours. After washing in order to remove the biological medium tested, the capacity of each of the three affinity supports to purify human FVII was measured. The results are given in table 10 below.

TABLE 10

|  | Support No. 1 after 100 hours of incubation in cryosupernatant | Support No. 1 after 100 hours of incubation in clarified milk |
|---|---|---|
| Start |  |  |
| FVII (OD280) mg | 17 | 17 |
| FVIIam IU | 13906 | 13906 |
| Not retained |  |  |
| FVII (OD280) mg | 9.3 | 10.2 |
| FVIIam IU | 496 | 192 |
| FVIIam/FVII:Ag yield | 0.027 | 0.009 |
| FVII yield (OD) % | 54.6 | 60.2 |
| FVIIam yield % | 3.6 | 1.4 |

TABLE 10-continued

|  | Support No. 1 after 100 hours of incubation in cryosupernatant | Support No. 1 after 100 hours of incubation in clarified milk |
|---|---|---|
| Eluate |  |  |
| FVII (OD280) mg | 7.3 | 7.1 |
| FVIIam IU | 12605 | 13180 |
| FVIIam/FVII:Ag ratio | 0.87 | 0.93 |
| FVII yield (OD) % | 42.6 | 41.8 |
| FVIIam yield % | 90.6 | 94.8 |

The results of table 10 show that the incubation of an affinity support as defined in the present description with biological media which represent starting products for purifying human FVII, for a very long period of time (100 hours), does not cause any significant change in the capacity of said support to purify human FVII.

7.6. Resistance of Affinity Supports to the Performing of Successive Purification Cycles The resistance of affinity support No. 3 prepared as described in section 7.1. above to undergo successive cycles of human FVII purification was tested.

Each purification cycle comprised the following steps:

equilibration of the affinity support in TP4 buffer (5 times the volume of the affinity support), simulation of bringing into contact with the composition to be purified: injection of TP4 buffer (5 times the volume of the affinity support), elution with the elution buffer (5 times the volume of the affinity support), sanitization with a 1M NaOH solution for 10 minutes (5 times the volume of the affinity support), and re-equilibration of the affinity support with the TP4 buffer (10 times the volume of the affinity support).

15 or 30 purification cycles above were respectively carried out with affinity support No. 3, and the capacity of said support, at the end of the 15 or 30 cycles, to purify human FVII was determined. The results are represented in table 11 below.

TABLE 11

|  | Affinity support No. 3 - 15 cycles | Affinity support No. 3 - 30 cycles |
|---|---|---|
| Start |  |  |
| FVII (OD280) mg | 15 | 15 |
| Not retained |  |  |
| FVII (OD280) mg | 7.2 | 6.5 |
| FVII yield (OD) % | 48.3 | 43.1 |
| Eluate |  |  |
| FVII (OD280) mg | 6.5 | 6.2 |
| FVII yield (OD) % | 43.0 | 41.0 |

The results of table 11 show that the capacity of an affinity support as defined in the present description to purify human FVII is unchanged, even after at least 30 cycles of implementation of a process mimicking the purification of a target protein.

TABLE 12

List of sequences

| SEQ ID No. | Description |
| --- | --- |
| SEQ ID No. 1 | Mapt 2CS aptamer |
| SEQ ID No. 2 | Mapt 1.2 aptamer |
| SEQ ID No. 3 | Mapt 2.2CS aptamer |

TABLE 12-continued

List of sequences

| SEQ ID No. | Description |
| --- | --- |
| SEQ ID No. 4 | Mapt anti-FIXa RNA aptamer |
| SEQ ID No. 5 | Mapt 1.2CSO aptamer |

The invention claimed is:

1. A process for immobilizing nucleic ligands on a solid support for chromatography, comprising the following steps:
   a) providing a solid support comprising a surface, wherein the solid support is selected from the group consisting of silica gels, polysaccharide gels, acrylamide gels, methacrylate gels, and polystyrene surfaces, and
   wherein the surface of the solid support comprises activated carboxylic acid groups in the form of N-hydroxysuccinimidyl ester groups of the following formula:

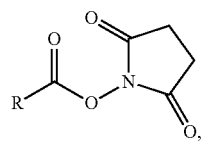

wherein R is the solid support,
   b) providing a nucleic ligand of formula (I):

NH$_2$-[SPAC]$_n$-[NUCL]                                     (I)

wherein:
   n is 1 or 0,
   [SPAC] is a spacer chain, and
   [NUCL] is a nucleic acid aptamer moiety which binds specifically to a target protein,
   said nucleic acid aptamer moiety having a length of 5 to 120 nucleotides,
   c) covalently coupling said nucleic ligand on the solid support by reacting the NH$_2$ of formula (I) with the activated carboxylic acid groups of the solid support at a pH ranging from 3.5 to 4.5, to immobilize the nucleic ligand on the solid support by an amide bond,
   wherein steps a) and b) may be in any order preceding step c), and
   wherein the resulting solid support is provided in a chromatography column suitable for protein purification.

2. The process as claimed in claim 1, wherein the coupling step is carried out at a temperature ranging from 0° C. to 35° C.

3. The process as claimed in claim 1, wherein the spacer chain is selected from the group consisting of C2-C20 linear alkyls and C2-C20 polyethylene glycols.

4. The process as claimed in claim 1, wherein the solid support is selected from the group consisting of silica gels, dextran gels, agarose gels, crosslinked agarose gels, and derivatives thereof.

5. The process as claimed in claim 1, wherein step c) further comprises:
   continuing the covalent coupling of said nucleic ligand with the activated carboxylic acid groups present at the surface of said solid support, under conditions where the pH is greater than 7.5.

6. The process as claimed in claim 1, wherein step c) is followed by a step d) of blocking the coupling reaction.

7. The process as claimed in claim 1, wherein the solid support is a polysaccharide gel.

* * * * *

SEQUENCE LISTING

```
<160> NUMBER OF SEQ ID NOS: 5

<210> SEQ ID NO 1
<211> LENGTH: 45
<212> TYPE: DNA
<213> ORGANISM: artificial sequence
<220> FEATURE:
<223> OTHER INFORMATION: aptamer

<400> SEQUENCE: 1
atgcagccag ccgcagtgta agtgaatgca gacatggtct aagtg            45

<210> SEQ ID NO 2
<211> LENGTH: 43
<212> TYPE: DNA
<213> ORGANISM: artificial sequence
<220> FEATURE:
<223> OTHER INFORMATION: aptamer

<400> SEQUENCE: 2
cgcacatgac ttgaagtaaa acgcgaatta cagaccaaac ccg              43

<210> SEQ ID NO 3
<211> LENGTH: 44
<212> TYPE: DNA
<213> ORGANISM: artificial sequence
<220> FEATURE:
<223> OTHER INFORMATION: aptamer

<400> SEQUENCE: 3
ccgcacgcta cgcgcatgaa cccgcgcaca cgacttgaag tagc             44

<210> SEQ ID NO 4
<211> LENGTH: 34
<212> TYPE: RNA
<213> ORGANISM: artificial sequence
<220> FEATURE:
<223> OTHER INFORMATION: aptamer
<220> FEATURE:
<221> NAME/KEY: misc_RNA
<222> LOCATION: (3)..(6)
<223> OTHER INFORMATION: 2'-fluoro ribosyl
<220> FEATURE:
<221> NAME/KEY: misc_RNA
<222> LOCATION: (8)..(8)
<223> OTHER INFORMATION: 2'-fluoro ribosyl
<220> FEATURE:
<221> NAME/KEY: misc_RNA
<222> LOCATION: (13)..(14)
<223> OTHER INFORMATION: 2'-fluoro ribosyl
<220> FEATURE:
<221> NAME/KEY: misc_RNA
<222> LOCATION: (15)..(15)
<223> OTHER INFORMATION: 2'-fluoro ribosyl
<220> FEATURE:
<221> NAME/KEY: misc_RNA
<222> LOCATION: (16)..(16)
<223> OTHER INFORMATION: 2'-fluoro ribosyl
<220> FEATURE:
<221> NAME/KEY: misc_RNA
```

```
<222> LOCATION: (17)..(17)
<223> OTHER INFORMATION: 2'-fluoro ribosyl
<220> FEATURE:
<221> NAME/KEY: misc_RNA
<222> LOCATION: (22)..(22)
<223> OTHER INFORMATION: 2'-fluoro ribosyl
<220> FEATURE:
<221> NAME/KEY: misc_RNA
<222> LOCATION: (23)..(23)
<223> OTHER INFORMATION: 2'-fluoro ribosyl
<220> FEATURE:
<221> NAME/KEY: misc_RNA
<222> LOCATION: (25)..(25)
<223> OTHER INFORMATION: 2'-fluoro ribosyl
<220> FEATURE:
<221> NAME/KEY: misc_RNA
<222> LOCATION: (26)..(27)
<223> OTHER INFORMATION: 2'-fluoro ribosyl
<220> FEATURE:
<221> NAME/KEY: misc_RNA
<222> LOCATION: (29)..(32)
<223> OTHER INFORMATION: 2'-fluoro ribosyl

<400> SEQUENCE: 4
auggggacua uaccgcguaa ugcugccucc ccau                           34

<210> SEQ ID NO 5
<211> LENGTH: 40
<212> TYPE: DNA
<213> ORGANISM: artificial sequence
<220> FEATURE:
<223> OTHER INFORMATION: aptamer

<400> SEQUENCE: 5
ccacgacctc gcacatgact tgaagtaaaa cgcgaattac                     40
```